US011246489B2

United States Patent
Lee et al.

(10) Patent No.: US 11,246,489 B2
(45) Date of Patent: Feb. 15, 2022

(54) ELECTRONIC DEVICE, MOBILE TERMINAL AND CONTROL METHOD THEREOF

(71) Applicant: SAMSUNG ELECTRONICS CO., LTD., Suwon-si (KR)

(72) Inventors: Anthony Chien-der Lee, Houston, TX (US); Joaquin Sanchez Duarte, Seoul (KR); Young-hyun Kim, Suwon-si (KR); Jae-geol Cho, Yongin-si (KR); Gun-woo Jin, Suwon-si (KR); Ah-young Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 451 days.

(21) Appl. No.: 16/075,860

(22) PCT Filed: Dec. 15, 2016

(86) PCT No.: PCT/KR2016/014684
§ 371 (c)(1),
(2) Date: Aug. 6, 2018

(87) PCT Pub. No.: WO2017/135564
PCT Pub. Date: Aug. 10, 2017

(65) Prior Publication Data
US 2019/0038135 A1 Feb. 7, 2019

(30) Foreign Application Priority Data
Feb. 5, 2016 (KR) .................. 10-2016-0015310

(51) Int. Cl.
*A61B 5/00* (2006.01)
*A61B 3/14* (2006.01)
(Continued)

(52) U.S. Cl.
CPC .......... *A61B 5/0077* (2013.01); *A61B 1/227* (2013.01); *A61B 3/10* (2013.01); *A61B 3/12* (2013.01);
(Continued)

(58) Field of Classification Search
CPC ... A61B 1/227; A61B 2560/0443; A61B 3/10; A61B 3/12; A61B 3/1208; A61B 3/145;
(Continued)

(56) References Cited

U.S. PATENT DOCUMENTS

| 2012/0320340 A1 | 12/2012 | Coleman, III |
| 2014/0085603 A1 | 3/2014 | Su et al. |
| 2014/0243685 A1 | 8/2014 | Patwardhan et al. |

FOREIGN PATENT DOCUMENTS

| CN | 203883900 U | 10/2014 |
| KR | 10-2012-0022050 A | 3/2012 |

(Continued)

OTHER PUBLICATIONS

Search Report dated Mar. 29, 2017 by the International Searching Authority in counterpart International Patent Application No. PCT/KR2016/014684. (PCT/ISA/210).
(Continued)

*Primary Examiner* — Michael T Rozanski
(74) *Attorney, Agent, or Firm* — Sughrue Mion, PLLC

(57) ABSTRACT

Disclosed is an electronic apparatus comprising a mounting portion to which one of a plurality of optical heads is selectively mountable; a communicator configured to communicate with an external apparatus; an optical module (optical unit) configured to transmit light, which is reflected from a user's body and passed through the optical head mounted to the mounting portion, to the external apparatus; and a controller configured to obtain identification information about the optical head mounted to the mounting portion
(Continued)

when one of the plurality of optical heads is mounted to the mounting portion, and control the communicator to transmit the identification information to the external apparatus. Thus, a desired optical head is mounted as necessary to capture an image of a user's body part, analyze the captured image, and provide analysis information to a user.

12 Claims, 39 Drawing Sheets

(51) Int. Cl.
    *A61B 3/12*     (2006.01)
    *A61B 1/227*     (2006.01)
    *A61B 3/10*     (2006.01)

(52) U.S. Cl.
    CPC ............ *A61B 3/1208* (2013.01); *A61B 3/145* (2013.01); *A61B 5/00* (2013.01); *A61B 5/441* (2013.01); *A61B 5/6898* (2013.01); *A61B 2560/0443* (2013.01)

(58) Field of Classification Search
    CPC ......... A61B 5/00; A61B 5/0077; A61B 5/441; A61B 5/6898
    See application file for complete search history.

(56) References Cited

FOREIGN PATENT DOCUMENTS

| | | |
|---|---|---|
| KR | 10-2013-0074316 A | 7/2013 |
| KR | 10-1420799 A | 7/2014 |
| KR | 10-2015-0045792 A | 4/2015 |
| WO | 2014/105649 A1 | 7/2014 |

OTHER PUBLICATIONS

Written Opiniont dated Mar. 29, 2017 by the International Searching Authority in counterpart International Patent Application No. PCT/KR2016/014684. (PCT/ISA/237).

ELECTRONIC DEVICE, MOBILE TERMINAL AND CONTROL METHOD THEREOF

This is a National Stage Application of PCT/KR2016/014684 filed Dec. 15, 2016, which claims priority to Korean Application No. 10-2016-0015310 filed Feb. 5, 2016, the disclosures of which are hereby incorporated by reference in their entireties.

TECHNICAL FIELD

The present invention relates to an electronic apparatus, a portable terminal and a control method thereof, and more particularly to an electronic apparatus, a portable terminal and a control method thereof, in which a plurality of optical heads is used to capture an image of a user's body part.

BACKGROUND ART

With development of electronic technology, various types of electronic products have been developed and spread. In particular, various display apparatuses such as a television (TV), a mobile phone, a personal computer (PC), a notebook computer, a personal digital assistant (PDA), etc. have been used a lot in most homes. Besides, functions of measuring a user's biometric signal and diagnosing the user' health conditions based on the measured biometric signal have been implemented in various electronic apparatuses.

In particular, such diagnosis apparatuses are generally manufactured individually in accordance with what they measure and what the type of the biometric signal is, and some of them have a function of transmitting measurement results through wired/wireless communication. Further, software is present to store and analyze measurement results respectively received from the diagnosis apparatuses.

DISCLOSURE

Technical Problem

However, some of independent diagnosis apparatuses may not support a communication function. Although the diagnosis apparatuses support the communication function, they use different kinds of software. Thus, separate purchases and maintenances are needed for all kinds of required diagnosis apparatuses, and it is also inconvenient to individually manage the software corresponding to each diagnosis apparatus.

Further, in cases of otitis media, dermatitis and the like symptoms of which progress are observable with eyes, it does not take long time to make a diagnosis, but a patient spends much time going to and from the hospital since the patient has to always go to the hospital and see a doctor. Furthermore, the hospital is overcrowded with patients.

Technical Solution

An aspect of the present invention is achieved by providing an electronic apparatus comprising: a mounting portion to which one of a plurality of optical heads is selectively mountable; a communicator configured to communicate with an external apparatus; an optical module (optical unit) configured to transmit light, which is reflected from a user's body and passed through the optical head mounted to the mounting portion, to the external apparatus; and a controller configured to obtain identification information about the optical head mounted to the mounting portion when one of the plurality of optical heads is mounted to the mounting portion, and control the communicator to transmit the identification information to the external apparatus.

Preferably, the controller may perform communication pairing with the external apparatus though the communicator when the electronic apparatus and the external apparatus are close to each other within a preset range, and transmit the identification information of the optical head mounted to the mounting portion to the external apparatus through the communicator when the communication pairing is completed.

Preferably, the electronic apparatus may further comprise a display, wherein the controller controls the display to display information about a current state of the electronic apparatus.

Preferably, the information about the current state of the electronic apparatus may comprise at least one of information about whether the electronic apparatus is communicating with the external apparatus and information about the optical head mounted to the mounting portion.

Preferably, the mounting portion may comprise a connection terminal for connecting with the mounted optical head, and the controller may receive the identification information from the mounted optical head through the connection terminal.

Preferably, the optical module may comprise a lens section comprising a plurality of lenses for transmitting incident light; and a lens control section configured to adjust a focal length of the lens section, wherein the controller controls the lens control section to adjust the focal length of the lens section in response to a control signal received from the external apparatus.

Preferably, the focal length of the lens section may be adjusted by at least one of change in distance between the plurality of lenses, and replacement of the lens being in use by another lens different in thickness, size and refractive index.

Preferably, the optical module may comprise a light source configured to generate light and output the light through the mounted optical head, and the controller may control the light source to generate and provide the light.

Preferably, the controller may control the light source to adjust at least one of brightness and chromaticity of the generate light.

Preferably, the controller may control the light source based on the control signal received from the external apparatus.

Preferably, the optical module may comprise a pattern generator to apply a pattern to the light generated by the light source, and the controller may control the pattern generator to apply the pattern to the light.

An aspect of the present invention is achieved by providing a method of controlling an electronic apparatus comprising a mounting portion to which one of a plurality of optical heads is selectively mountable, the method comprising: mounting one of the plurality of optical heads to the mounting portion; communicating with an external apparatus; obtaining identification information of the mounted optical head and transmitting the identification information to the external apparatus; and transmitting light reflected from a user's body and passed through the mounted optical head to the external apparatus.

Preferably, the communicating with the external apparatus may comprise performing communication pairing with the external apparatus though the communicator when the electronic apparatus and the external apparatus are close to each other within a preset range; and transmitting the identification information of the optical head mounted to the mounting portion to the external apparatus through the communicator when the communication pairing is completed.

Preferably, the method may further comprise displaying information about a current state of the electronic apparatus through the display.

Preferably, the information about the current state of the electronic apparatus may comprise at least one of information about whether the electronic apparatus is communicating with the external apparatus and information about the optical head mounted to the mounting portion.

Preferably, the transmitting light reflected from a user's body part to the external apparatus may comprise transmitting incident light through a lens section comprising a plurality of lenses; and adjusting a focal length of the lens section in response to a control signal received from the external apparatus.

Preferably, the adjusting the focal length of the lens section comprises at least one of changing in distance between the plurality of lenses, and replacing the lens being in use by another lens different in thickness, size and refractive index.

Preferably, the method may further comprise generating and outputting light through the mounted optical head.

Preferably, the generating and outputting the light through the mounted optical head may comprise adjust at least one of brightness and color of the generate light.

Preferably, the generating and outputting the light through the mounted optical head may comprise generating the light based on a control signal received from the external device.

Preferably, the generating and outputting the light through the mounted optical head may comprise apply a pattern to the generated light.

An aspect of the present invention is achieved by providing a portable terminal comprising a display configured to output an image; an image capturing module to which a plurality of optical heads is mountable; a communicator configured to communicate with a detachably mountable image capturing module and other external apparatus; a camera configured to capture an image of a user's body part; and a controller configured to control the display to provide a UI including a plurality of diagnosis items, control the communicator to transmit a first control signal to the optical module so as to capture the image of the user's body part based on the identification information of the optical head and a user's selection through the UI, capture the user's body part based on light reflected from the user's body part through the optical module, and control the display to display the captured image Preferably, the controller may control the display to display the information about the needed optical head so as to mount the needed optical head to the optical module when it is determined based on the received identification information of the mounted optical head and the diagnosis item selected by a user that the mounted optical head is mismatched with the optical head needed for the diagnosis.

Preferably, the information about the needed optical head may comprise at least one of a manufacturer, a serial number and an outer appearance of the needed optical head.

Preferably, the controller may control the communicator to transmit the captured image to the external apparatus.

Preferably, the controller may control the display to provide information about a second control signal to a user when the second control signal for making a diagnosis is received from the outside.

Preferably, the controller may control the display to display the information about the needed optical head so as to mount the needed optical head to the optical module when it is determined based on the received identification information of the mounted optical head and the second control signal received from the outside that the mounted optical head is mismatched with the optical head needed for the diagnosis.

Preferably, the controller may provide guide information so that the user can correctly capture an image of the user's body part based on the diagnosis item selected by the user.

Preferably, the guide information may include information about a distance from the user's body part, a focus, an angle, etc.

Preferably, the controller may control the display apparatus to blurredly display the previously captured image based on the selected diagnosis item and display the captured image of the user's body part along with the blurredly displayed captured image in real time, and the guide information may include information about a matching degree by comparison between the blurredly displayed previously captured image and the image of the user's body part captured in real time.

Preferably, the controller may analyze the captured image and provide diagnosis information based on analysis information.

Preferably, the diagnosis information may include information about the user's body part.

An aspect of the present invention may be achieved by providing an electronic apparatus comprising: a mounting portion to which one of a plurality of optical heads is selectively mountable; a communicator configured to communicate with an external apparatus; a camera configured to capture an image of a user's body part; and a controller configured to control the communicator to obtain identification information of the optical head mounted to the mounting portion when one of the plurality of optical heads is mounted to the mounting portion and transmit the obtained identification information to the external apparatus, control the camera to capture an image of the user's body part through the mounted optical head in response to a control command received from the external apparatus, and control the communicator to transmit the captured and generated image to the external apparatus.

Advantageous Effects

As described above, according to the present invention, one of various optical heads is selectively mounted to an electronic apparatus as necessary and captures an image of a user's body part, and a captured image itself or an image signal electrically converted from the captured image is transmitted to a display apparatus, thereby making a diagnosis apparatus small and inexpensive. Further, it is possible to transmit the captured image to the hospital through a network without directly going to the hospital, thereby improving user convenience.

BEST MODE

Figure 1:
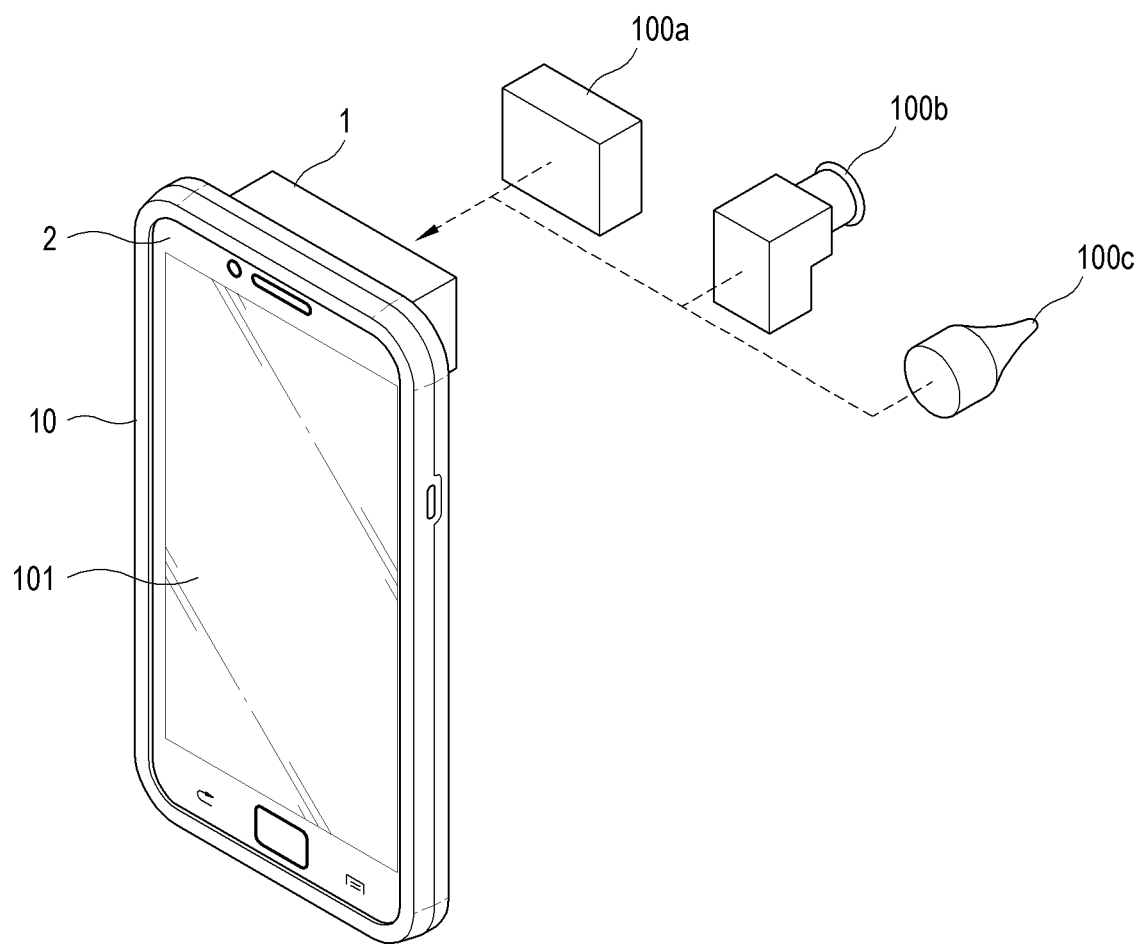
FIG. 1 illustrates an example of using an electronic apparatus and a portable terminal to which a plurality of optical heads is attachable according to one embodiment of according to one embodiment of the present invention.

Below, embodiments of the present invention will be described with reference to accompanying drawings. However, detailed descriptions about publicly known functions or configurations, which may cloud the gist of the present invention, will be omitted from the following descriptions and accompanying drawings. Further, like numerals refer to like elements throughout.

Terms or words used in the specification and claims set forth herein are not restrictively construed as typical or lexical meaning, but construed as meaning and concept corresponding to technical idea of the present invention on the principle that the inventor can properly define terms to describe his/her own invention in the best way. Thus, the embodiments disclosed in this specification and elements illustrated in the drawings are merely one preferred embodiment of the present invention, and do not fully represent the technical idea of the present invention. Accordingly, it will be understood that various equivalents and modifications can be made to replace these embodiments and elements at the point of time when the present invention is applied.

In the accompanying drawings, some elements are exaggerated, omitted or simplified, and the size of each element does not entirely reflect the actual size. The present invention is not limited to the relative size or space illustrated in the accompanying drawings.

When a certain element 'includes' another element throughout the specification, unless otherwise noted, it does not means that elements other than the included element are excepted, but means that the included elements are added. Further, A "portion" set forth herein refers to software or hardware such as FPGA or ASIC, and performs certain roles. However, the meaning of the "portion" is not limited to software or hardware. The "portion" may be configured to be present in a storage medium for addressing or may be configured to reproduce one or more processors. For example, the "portion" includes software elements, object-oriented software elements, class elements, task elements and the like elements, and processes, functions, attributes, procedures, subroutines, segments of a program code, drivers, firmware, a microcode, a circuit, data, a database, data structures, tables, arrays and variables. The function provided in the elements and the "portions" may be carried out by combining fewer elements and "portions" or subdividing additional elements and "portions".

Hereinafter, embodiments of the present invention will be described in detail with reference to the accompanying drawings so as to be easily materialized by a person having an ordinary skill in the art to which the present invention pertains. However, the present invention may be embodied in various different forms, but not limited to the embodiments set forth herein. Further, parts unrelated to the descriptions are omitted to clearly illustrate the present invention in the drawings, and like elements refer to like elements throughout.

In this specification, a display apparatus wirelessly receives power from an external apparatus, and is configured to provide an image based on a received image signal.

Figure 2:
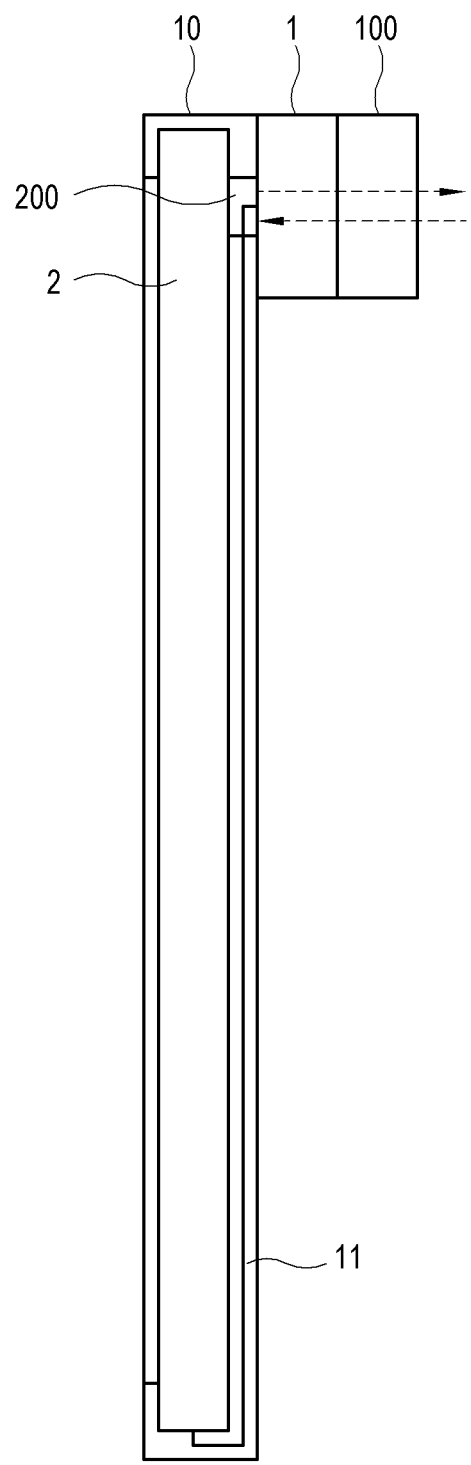
FIG. 2 illustrates an example of using an electronic apparatus and a portable terminal to which a plurality of optical heads is attachable according to one embodiment of according to one embodiment of the present invention.

FIGS. 1 and 2 illustrate examples of using an electronic apparatus and a portable terminal to which a plurality of optical heads is attachable according to one embodiment of according to one embodiment of the present invention.

A portable terminal 2 refers to an electronic apparatus such as a smart phone, a PDA or the like a user can carry, and is covered with a case 10. The case 10 is to protect the portable terminal 2 from an external shock, and the case 10 in this embodiment may be configured to couple with an electronic apparatus 1 and internally include signal wires 11 for connecting the terminals of the portable terminal 2 and the electronic apparatus 1 to supply power to the electronic apparatus 1 and receive information from the electronic apparatus 1.

The portable terminal 2 employs the electronic apparatus 1 coupling with one among a plurality of optical heads 100a, 100b and 100c to capture an image of a user's body part, and is configured to provide the captured image to a user through a display 101.

The electronic apparatus 1 is configured to couple with one among the plurality of optical heads 100a, 100b and 100c. The electronic apparatus 1 may be configured to provide identification information of the mounted optical heads 100a, 100b and 100c to the portable terminal 2 through the signal wire connected to the portable terminal 2 and wireless communication. The portable terminal 2 may offer a user information about the kind of mounted optical head 100a, 100b or 100c based on the received identification information. When a user confirms the information about the kind of mounted optical head 100a, 100b of 100c and controls a user interface (UI) of the portable terminal 2 to capture his/her body, light reflected from a user body is incident to the electronic apparatus 1 through the optical head 100a, 100b or 100c and the electronic apparatus 1 provides the incident light to the portable terminal 2. A camera of the portable terminal 2 converts light received from the electronic apparatus 1 into an image, and the portable terminal 2 displays the image on the display 101. The electronic apparatus 1 may include a light source configured to generate and emit light based on the identification information received from the mounted optical head 100a, 100b or 100c or a control signal received from the portable terminal 2.

For instance, the electronic apparatus 1 has a mounting portion to which the optical head 100c corresponding to an otoscope is attached for capturing the inner ear, and the portable terminal 2 receiving identification information of the optical head 100c corresponding to the otoscope from the electronic apparatus 1 transmits a control signal to the electronic apparatus 1 so that light can be output. The electronic apparatus 1 is configured to output the light emitted from the light source to a user's inner ear through the mounted optical head 100c, and provide the reflected and light received through the optical head 100c to the portable terminal 2.

The plurality of optical heads 100a, 100b and 100c may be various provided to capture an image of a user's body, and mounted to the electronic apparatus 1. For example, the plurality of optical heads 100a, 100b and 100c may include the optical head 100c corresponding to the otoscope, an optical head 100b corresponding to an ophthalmoscope, and an optical head 100a corresponding to a dermatoscope. The plurality of optical heads 100a, 100b and 100c are not limited to the drawings and the foregoing examples, and may be variously provided to measure a user's body parts.

Figure 3:
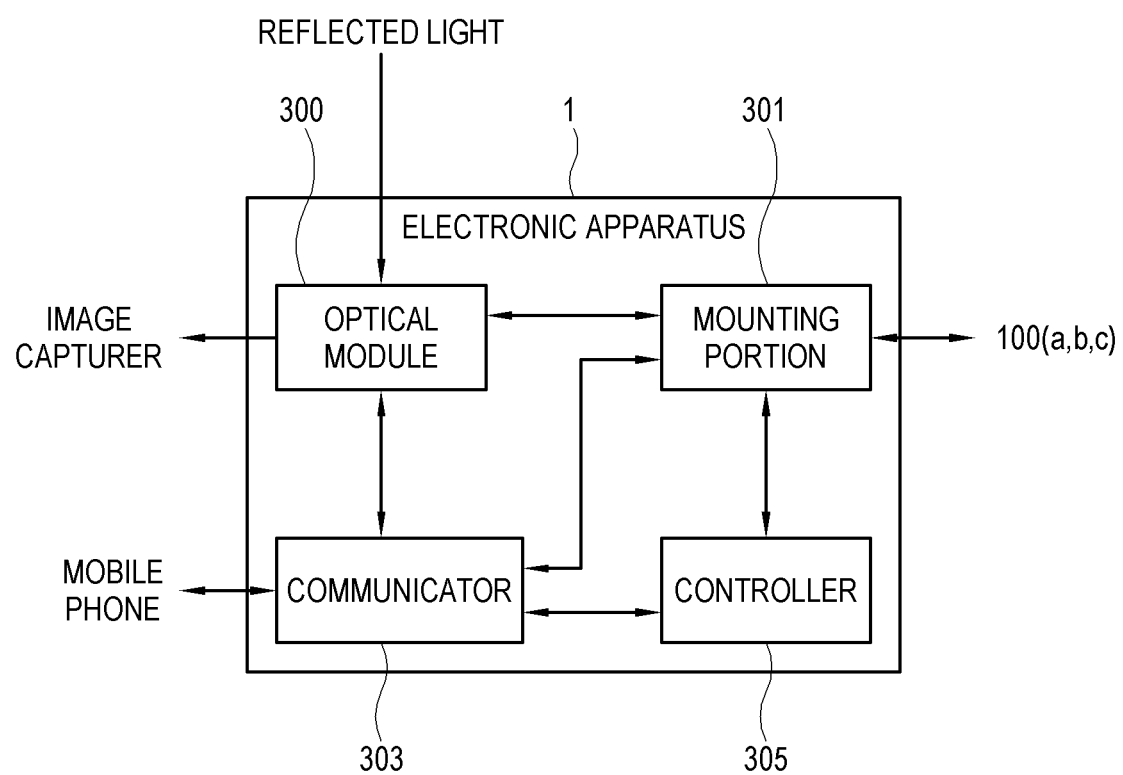
FIG. 3 is a block diagram of the electronic apparatus according to one embodiment of the present invention.

FIG. 3 is a block diagram of the electronic apparatus according to one embodiment of the present invention.

The electronic apparatus 1 includes a mounting portion 301, a communicator 303, an optical module 300, and a controller 305. Specifically, the electronic apparatus 1 performs a common operation regardless of the kinds of mounted optical heads 100a, 100b and 100c based on the control signal received from the external apparatus, i.e. the portable terminal 2, captures an image by supplying power to the optical head or based on the reflected light received from the optical head 100a, 100b or 100c, and transmits the captured image to the external apparatus 2. Such an electronic apparatus 1 detachably couples with at least one among the plurality of optical heads 100a, 100b and 100c, and may be materialized in various forms.

The mounting portion 301 is configured to selectively and detachably couple with at least one among the plurality of optical heads 100a, 100b and 100c which are different in the curvature or thickness of a lens provided therein, a distance between the lenses, etc. Specifically, the mounting portion 301 has a structure to be physically engaged with mounting portions of the optical heads 100a, 100b and 100c, and the mounting portion 301 may further include a connection terminal for exchanging power or data with the coupled optical head 100a, 100b or 100c. For example, the optical head 100a, 100b or 100c may be mounted to the electronic apparatus 1 as if a mounting portion of a camera lens is mounted to a mounting portion of a camera body. Further, the mounting portion 301 may couple with the mounting portion of the optical head 100a, 100b or 100c by not only such a physical structure but also a magnetic substance having magnetic force. However, the mounting portions may be coupled by various methods without limitations.

Here, the plurality of optical heads 100a, 100b and 100c may be configured to have different structures according to a user's body parts desired to be measured. Specifically, the optical heads 100a, 100b and 100c may be differently shaped corresponding to a user's body parts targeted for measurement, and may include sensing sections different according to body parts.

For example, in a case of the optical head 100*c* corresponding to the otoscope for examining an ear, a front opening portion for capturing an image may be narrower than those of the other optical heads 100*a* and 100*b*, and covered with a disposable speculum. Further, the optical head 100*b* corresponding to the ophthalmoscope for examining an eye is configured to observe an eye ground, a vitreous body, a crystalline lens, etc. More specifically, the optical head 100*b* corresponding to the ophthalmoscope may be configured to emit light from the electronic apparatus 1 to the eye ground, and receive light reflected from the eye ground. The optical head 100*b* is configured to capture an eye-ground image magnified by a factor of 4 to 16 in accordance with uses, and may employ lenses different according to the uses to examine an inverted image, an erect image, etc. of the eye ground. Further, the optical head 100*a* corresponding to the dermatoscope for examining a skin may be configured to examine dermatitis, skin cancer, etc. The optical head 100*a* corresponding to the dermatoscope is in contact with or arranged leaving a predetermined distance from a skin and captures a pigmented mole of the skin magnified by the minimum factor of 5 to the maximum factor of 20. The captured image of the pigmented mole of the skin is transmitted to the portable terminal 2, and the portable terminal 2 is configured to perform analysis such as measurement of the size of the pigmented mole and offer the relevant information to a user.

Further, the plurality of optical heads 100*a*, 100*b* and 100*c* may each include sensing sections for sensing temperature, humidity, etc. of body parts, and may be further materialized to include sensors for sensing biometric signals such as a brainwave, an electromyogram, a heart rate, etc. of a user.

The optical module 300 is configured to transmit light reflected from a user's body and passed through the mounted optical head 100*a*, 100*b* or 100*c* to the portable terminal 2. To this end, the optical module 300 may include a plurality of lens sections for transmitting incident light, a light source for emitting light in response to a control signal from the portable terminal 2, and a splitter for transmitting the incident light from the optical head 100*a*, 100*b* or 100*c* to the portable terminal 2. Details of the optical module 300 will be described later.

The communicator 303 is configured to communicate with an external apparatus. Here, the external apparatus refers to an electronic apparatus, i.e. the portable terminal 2, which generates an image by receiving light incident through the optical module 300, and makes the generated image be displayed, stored, analyzed, etc. As described above, the portable terminal 2 may be materialized by a complex electronic apparatus such as a smart phone, a PDA, a tablet PC, a laptop computer, a digital camera, or the like having a function of capturing an image.

The communicator 303 is provided to connect with other external apparatus, a network, etc., and includes a plurality of connection ports corresponding to various standards such as a high definition multimedia interface (HDMI), a universal serial bus (USB), etc. The communicator 303 may perform wired communication with a plurality of servers through a wired local area network (WLAN). Further, the communication performed in the communicator 303 may include wireless communication. The communicator 303 may include a radio frequency (RF) circuit for transmitting and receiving an RF signal to perform the wireless communication, and may be configured to perform communication based on one or more among Wi-Fi, Bluetooth, BLE, ANT, WiMAX, Z-Wave, ZigBee, ultra-Wide band (UWB), Wireless USB, Wireless HD, Wireless HART, near field communication (NFC), and radio frequency identification (RFID).

The communicator 303 may be configured to receive the identification information from the optical head 100*a*, 100*b* or 100*c* mounted to the mounting portion 301, provide the received identification information to the portable terminal 2, and receive the control signal from the portable terminal 2.

Further, the communicator 303 may include a power terminal to receive power from the portable terminal 2. The power terminal may be configured to receive power through a connected signal wire from a power terminal of the portable terminal 2, and may be configured to wirelessly receive power from the portable terminal 2.

For instance, the power terminal may be configured to further include a coil portion to wirelessly transmit and receive power by a magnetic induction principle that variance in a magnetic field induced by variance in electric current flowing in a transmitting coil causes electric current to flow in a receiving coil, and a converter to convert alternating current into a direct current. Further, the power terminal may be configured to wirelessly receive power by a magnetic resonance principle that a wireless power signal causes an electromagnetic resonance to induce an electric current and transmit power.

The electronic apparatus 1 may be further configured to convert light energy from a flash light into electric energy through a photocell.

The electronic apparatus 1 may further include a user command input section. The user command input section receives a user's command and transmits the received command to the controller 305, and the controller 305 controls operations of the electronic apparatus 1 in response to a user's control input to the user command input section. The user command input section may include a key button and the like provided on an outer side of the electronic apparatus 1, and may be materialized as a touch screen of the display.

A user may use the user command input section of the electronic apparatus 1 to control an output level of light emitted through the optical head 100 of the optical module 300; adjust color of an image; form and change a pattern for assisting examination; adjust a focus for an image to be captured; etc.

The controller 305 is configured to control general operations of the electronic apparatus 1. Specifically, the controller 305 obtains the identification information of the optical head 100*a*, 100*b* or 100*c* mounted through the mounting portion 301, and controls the communicator 303 to provide the obtained information to the portable terminal 2. Further, the controller 305 may control the optical module 300 to generate and output light based on the identification information of the mounted optical head 100*a*, 100*b* or 100*c* or the control signal provided by the portable terminal 2. For instance, when the mounted optical head 100*a*, 100*b* or 100*c* is the optical head 100*c* corresponding to the otoscope, light may be directly output by a user's intention of measuring an inner ear so that the reflected light can be transmitted to the portable terminal 2, or light may be output from time when a control signal for emitting light is received from the portable terminal 2. Further, information about a magnification of a captured image is transmitted based on a distance or the like between the lenses used in the optical head 100*c* corresponding to the otoscope, and used in determining the size of captured image.

The controller 305 may further adjust a focal length of the optical module 300 in response to a control signal received from the portable terminal 2 or the mounted optical head 100a, 100b or 100c. Since the plurality of optical heads 100a, 100b and 100c are different in the kinds of lens and the focal length in accordance with their uses, the focal length of the optical module 300 for transmitting light to the optical head 100a, 100b or 100c or receiving light from the optical head 100a, 100b or 100c may be differently adjusted according to the mounted optical head 100a, 100b or 100c. Further, when a user controls the portable terminal 2 or makes an input to the user command input section of the electronic apparatus 1 to zoom in or out an image, the focal length may be adjusted based on this control. In this case, the communicator 303 may be controlled to transmit information about the focal length and the magnification to the portable terminal 2.

The electronic apparatus 1 may further include a sensing section for sensing a distance and an angle from a user's body to the electronic apparatus 1, and the controller 305 may provide information about the distance and angle, which are sensed by the sensing section while an image is captured, to the portable terminal 2.

Figure 4:
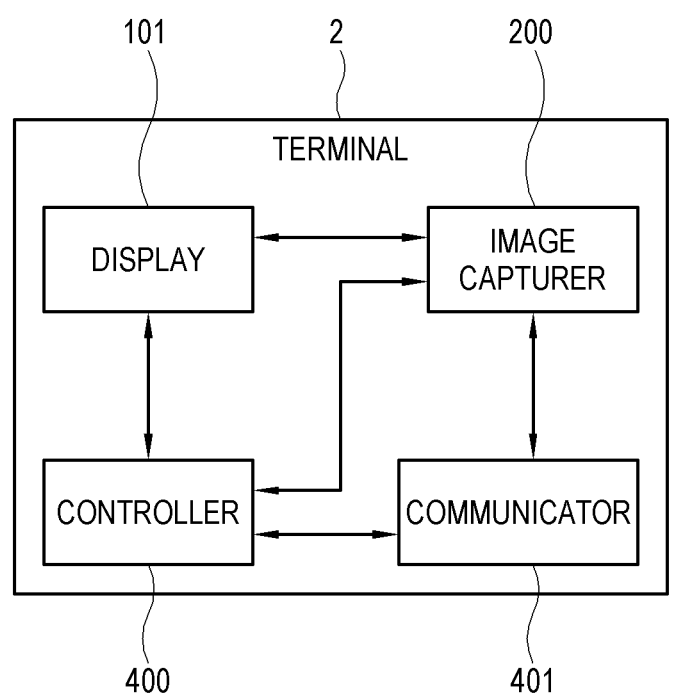
FIG. 4 is a block diagram of a portable terminal according to one embodiment of the present invention.

FIG. 4 is a block diagram of a portable terminal according to one embodiment of the present invention.

The portable terminal 2 is capable of communicating with the exterior, and showing information received through the communication to a user. The portable terminal 2 may include a display 101, a camera 200, a communicator 401, and a controller 400.

The display 101 is configured to display an image under control of the controller 400. The display 101 may include a display panel where an image is displayed, and a backlight unit as a light source for emitting light to the display panel, and may further include a driver for driving the display panel and the light source by supplying power thereto. When the display panel is a non-emissive device such as a liquid crystal display (LCD) or the like, an image is displayable with light emitted from the light source. When the display panel is a self-emissive device, a driving circuit is configured to directly supply power to electrodes of the self-emissive device in the display panel. The portable terminal 2 may further include a loudspeaker for outputting a sound or voice. The loudspeaker may be provided in the portable terminal 2, or may be materialized by an external apparatus connected by wired/wireless communication.

The display 101 may be configured to further include a touch screen for sensing a user's touch input to the display panel, and provide a UI of menu items corresponding to various functions to a user. The portable terminal 2 may be configured to provide a function corresponding to a user's touch input made on the UI. The UI provided by the portable terminal 2 and various functions corresponding to a user's touch input using the UI will be described later.

The camera 200 is configured to transmit a captured image to the display 101. The camera 200 may include the optical module having the lens, the image processor for sensing incident light and converting an image of an object focused on the lens into an image of an electric signal, etc. The image processor may include a charged coupled device (CCD).

The communicator 401 may communicate with the external apparatus. The external apparatus includes an other-party portable terminal 2 making a phone call to the portable terminal 2, a computing device capable of doing other communications, a server, an electronic apparatus 1 for providing light reflected from a user's body to the portable terminal 2 through the optical head 100. The communicator 401 may further include an antenna for receiving an image signal from the exterior, a tuner for processing the signal received through the antenna and providing image information, a demodulator, etc. The communicator 401 may be configured to receive at least one among a terrestrial broadcast signal, a satellite signal, and a cable signal. Further, the communicator 401 may receive a broadcast signal or the like through a digital broadcasting system such as digital multimedia broadcasting-terrestrial (DMB-T), digital multimedia broadcasting-satellite (DMB-S), media forward link only (MediaFLO), digital video broadcast-handheld (DVB-H), integrated services digital broadcast-terrestrial (ISDB-T), etc. The received broadcast signal is processed to be displayed as an image and then provided to the display 101, and the display 101 is configured to display an image based on the processed image signal.

The communicator 401 may be configured to directly receive data such as the identification information of the optical head 100 mounted to the electronic apparatus 1 from the electronic apparatus 1 and provide a control signal to the electronic apparatus 1, and may include a plurality of connection ports according to various standards such as HDMI, USB, etc. like the communicator of the electronic apparatus 1, and perform wired communication with a plurality of servers through a wired LAN. Further, the communicator 401 may include an RF circuit for transmitting and receiving an RF signal to perform wireless communication, and perform communication based one or more among Wi-Fi, Bluetooth, BLE, ANT, WiMAX, Z-Wave, ZigBee, UWB, Wireless USB, Wireless HD, Wireless HART, NFC, and RFID.

The communicator 401 may further include a power terminal to transmit power to the coupled electronic apparatus 1, and the power terminal may be configured to transmit power by a wire or wirelessly.

The controller 400 may be configured to control general operations of the portable terminal 2 according to the present invention. More specifically, the controller 400 is configured to control the elements of the portable terminal 2 so as to make the portable terminal 2 communicate with the external apparatuses, provide information based on a received signal and data to a user, and provide at least one among a plurality of functions supported in the portable terminal 2 to a selected user in response to a user's input.

The plurality of functions supported in the portable terminal 2 may include a medical examination service of examining a user's health conditions, and providing information based on the measured health conditions. The medical examination service refers to a service of capturing an image of a user's body part, analyzing the captured image, and providing diagnosis information to the user. The controller 400 may offer guide information to a user so as to capture the user's body part, and transmit the captured image to an external display apparatus to display an enlarged image or transmit the captured image to the hospital or the like outside so that a user can receive a telemedicine service.

The portable terminal 2 according to one embodiment of the present invention is configured to capture an image of a user's body part through the camera 200, predict a disease or analyze a recovered degree or the like through the captured image, and provide prediction or analysis to a user.

For instance, dermatitis or skin cancer may be predicted by checking change in the size of mole on a user's skin; otitis media is determined using an inner ear image; and the captured image makes it possible to analyze whether a skin wound or the like heals over.

The controller 400 directly analyzes the image and provides relevant information to a user; transmits the captured image to the display apparatus to display the image largely; or performs a series of operations to provide the image to the hospital or the like through the network.

The medical examination service may start when a user selects the medical examination service to start among the plurality of functions, when a user mounts one among the plurality of optical heads 100a, 100b and 100c to the electronic apparatus 1, or when a capturing request is received from the hospital or the like.

When the medical examination service starts in response to a user's selection or the capturing request from the outside, the controller 400 may offer a user the guide information about what is the optical head 100 to be mounted, a user's body to be captured, a distance and angle needed to be kept between the user's body and the portable terminal 2, etc. When a user mounts the optical head 100 based on the guide information, it is determined based on the identification information received from the mounted optical head 100 whether the optical head 100 is mounted matching with the starting medical examination service. When it is determined that the mounted optical head 100 does not match with the medical examination service started by a user, the guide information may be provided again to make a user mount the matching optical head 100.

Further, when a user mounts the optical head 100 to the electronic apparatus 1, information about what kinds of the optical head 100 and the electronic apparatus 1 is transmitted to the portable terminal 2, so that a corresponding control program can be automatically loaded, thereby increasing user convenience. That is, when the optical head 100c corresponding to the otoscope is mounted to the electronic apparatus 1, the portable terminal 2 may execute a control program for examining an ear, and provide the guide information or the like UI for examining a user's ear to the user through the display 101.

Further, the portable terminal 2 may load a control program different according to the kind of mounted electronic apparatus 1. Although the same optical head 100 is used, a user may be provided with services different according to the kind of electronic apparatus 1. Not only the kind of optical head 100 but also the information about the electronic apparatus 1 mounted to the portable terminal 2 is also transmitted to the portable terminal 2 so that relevant control program is loaded. For instance, when the optical head 100c corresponding to the otoscope is mounted to a general electronic apparatus 1, only the control program for capturing internal/middle ear images is loaded. On the other hand, when the optical head 100c is mounted to the electronic apparatus 1 having a thermometer or the like, not only an image is captured but also a body temperature is measured, and a control program for offering information about measured body temperature to a user is loaded. Therefore, a user does not have to find a program for properly using the electronic apparatus 1 and intuitively grasps what functions the mounted electronic apparatus 1 and optical head 100 perform, thereby improving user convenience and usability.

When the medical examination service starts as a user mounts the optical head 100 to the electronic apparatus 1, the identification information of the optical head 100 is provided to the portable terminal 2 via the electronic apparatus 1, and the controller 400 informs a user that the medical examination service starts and provides the guide information for capturing a body part to a user, similarly to selection of a user through the UI.

The controller 400 may also provide the guide information so that a user can correctly take an image of his/her body part. The guide information may include information about a distance from a user's body part to be captured, a capturing angle of the portable terminal 2, etc. In particular, when a user takes images of a mole, wound or the like on his/her skin leaving a time lag, the mole, wound or the like have to be captured at a position similar to a previous position in order to correctly analyze change in the size of skin mole or wound. The controller 400 may control the loudspeaker to provide a notification sound when a user puts the portable terminal 2 at the same distance and angle as those of previous capturing with reference to the guide information, and a warning sound when a user puts the portable terminal 2 at a wrong position. Further, the controller 400 may control the display 101 to display a previously captured image overlapping with a currently capturing image so that a user can takes an image at a correct position.

The controller 400 may also control the display 101 to display a captured user body image, and provide the captured image to the external display apparatus or transmit the captured image to the hospital or the like outside via the network as described above.

Figure 5:
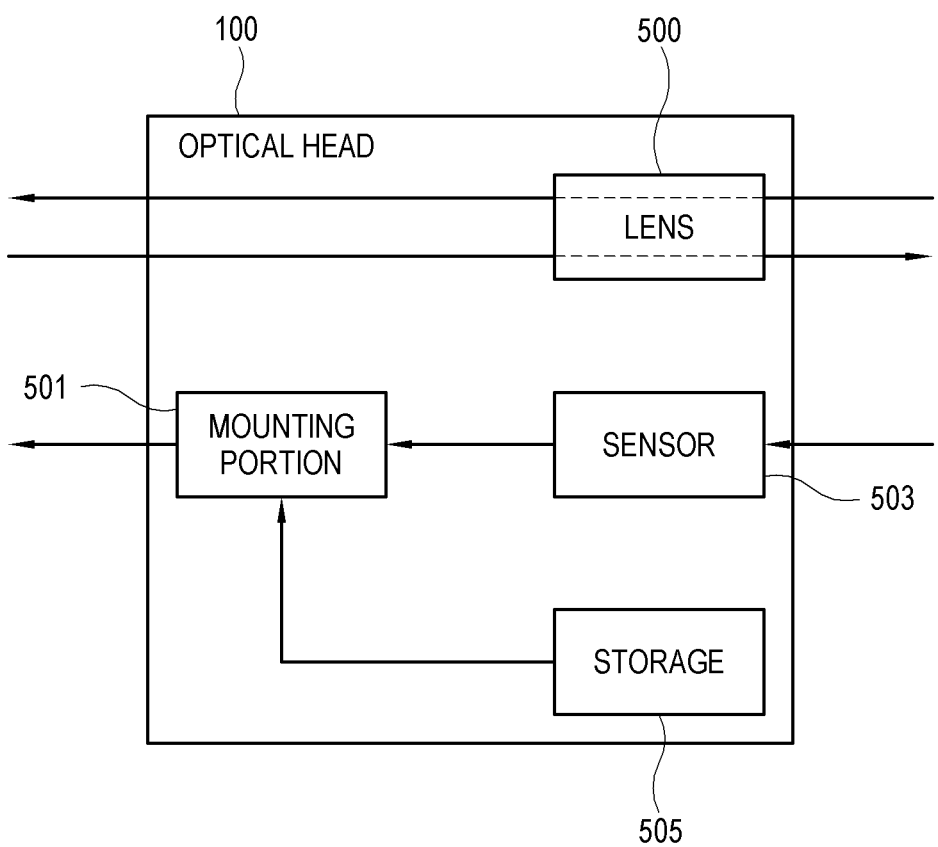
FIG. 5 is a block diagram of an optical head according to one embodiment of the present invention.

FIG. 5 is a block diagram of an optical head according to one embodiment of the present invention.

The optical head 100 is formed to have an outer appearance different as necessary, and mounted to the electronic apparatus 1. The optical head 100 may further include a lens section 500 and a mounting portion 501. The optical head 100 may be configured to operate with power received from the electronic apparatus 1 through the mounting portion 501, and transmit light reflected from a user's body to the electronic apparatus 1. The optical head 100 may further include a storage 505 for storing the identification information of each optical head 100, and a sensing section 503 for sensing biometric information of a user's body.

The lens section 500 is configured to make light output from the electronic apparatus 1 travel to a user's body, and incident light reflected from the user's body travel to the electronic apparatus 1. The lens section 500 may include a plurality of lenses, which are different in focal length in accordance with the kinds of optical head 100, and thus the optical heads 100 are different in the size of lens, a distance between the lenses, the thickness of the lens, a refractive index, optical coating, polarization axis, etc.

The mounting portion 501 is configured to make the optical head 100 be detachably mounted to the electronic apparatus 1. The mounting portion 501 has a structure to be physically engaged with the mounting portion of the electronic apparatus 1, and includes a connection terminal for providing the identification information of the optical head 100 to the electronic apparatus 1. The mounting portion 501 may also couple with the mounting portion of the electronic apparatus 1 by a magnetic substance having magnetic force as described above.

The storage 505 may be configured to store the identification information of the optical head 100. The storage 505 may be materialized by a nonvolatile memory (i.e. a writable read only memory, ROM) which retains data even though power supplied to the optical head 100 is cut off, and reflects changes. That is, the storage 505 may be materialized by one among a flash memory, EPROM and EEPROM. The storage 505 may include information about the lens section 500, such as the kind, a manufacturer, a serial number, optical filters, polarization axis, the refractive index and magnification of the lens, etc.

The sensing section 503 may be configured to sense a user's biometric signal. More specifically, in a case of the optical head 100 corresponding to the otoscope to be inserted in a user's inner ear, the sensing section 503 may be configured to obtain a user's brainwaves, that is, an electroencephalogram (EEG), an electrooculogram (EOG), etc. Further, the sensing section 503 may be configured to contact a user's body and obtain various pieces of information, such as temperature, humidity, etc. of the user's body. The information obtained by sensing a user's body through the sensing section 503 may be stored in the storage 505 or transmitted to the electronic apparatus 1 through the mounting portion 501. The information transmitted to the electronic apparatus 1 is transmitted to the portable terminal 2. In this case, the information may be encrypted and then stored to protect sensitive medical information.

Figure 6:
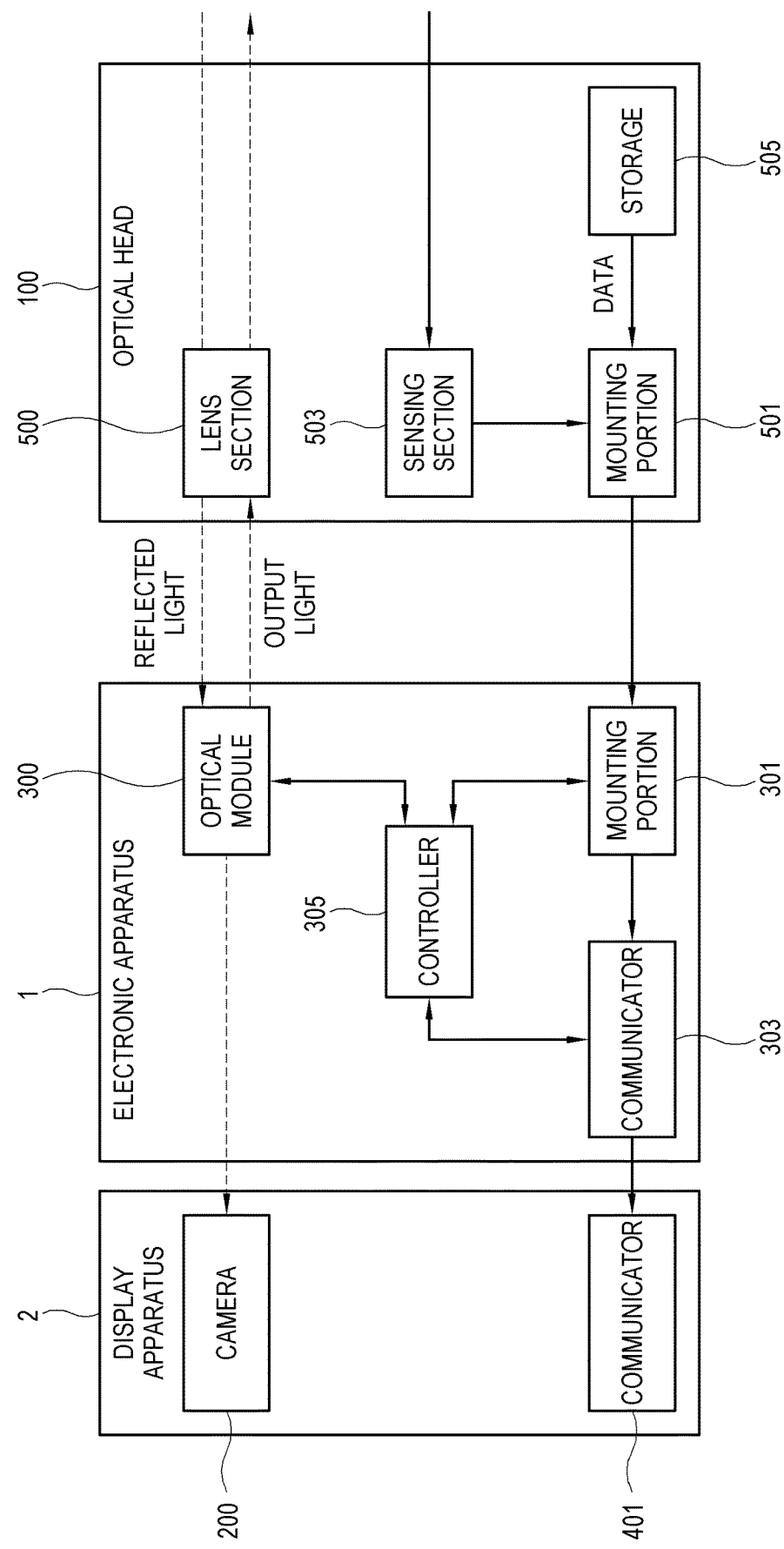
FIG. 6 is a block diagram of illustrating operations of the portable terminal, the electronic apparatus and the optical head.

FIG. 6 is a block diagram of illustrating operations of the portable terminal, the electronic apparatus and the optical head.

The portable terminal 2 and the electronic apparatus 1 are coupled so that the electronic apparatus 1 can operate with power received from the portable terminal 2. When the mounting portion 501 of the optical head 100 is mounted to the mounting portion 301 of the electronic apparatus 1, the electronic apparatus 1 receives the identification information from the optical head 100, and transmits the received identification information to the portable terminal 2.

The portable terminal 2 may make the display 101 provide the guide information for guiding a user to take an image of his/her body part based on the identification information of the optical head 100 mounted to the electronic apparatus 1. The guide information includes information about the mounted optical head 100, and information for allowing a user to take an image of his/her body part, such as a posture for capturing an image of a body part, a distance, angle, etc. between the body part and the electronic apparatus 1, etc. In this case, the angle of the portable terminal 2 is sensed by an accelerometer, a gyroscope, and a geomagnetic sensor provided in the portable terminal 2, and compared with the angle of the portable terminal 2 at the previous capturing, thereby providing relevant information to a user.

The electronic apparatus 1 transmits light reflected from a user's body to the camera 200 of the portable terminal 2 through the optical head 100, and the camera 200 converts the received light into an image having an electric signal and transmits the image to the display 101. The portable terminal 2 may provide a captured image and information obtained by analyzing the image to a user through the display 101, and may also transmit the captured image to the external apparatus.

According to another embodiment, the electronic apparatus 1 may generate and output light in response to a control signal received from the portable terminal 2. The output light is emitted to a user's body through the optical head 100, and the light reflected from a user's body is also incident to the electronic apparatus 1 through the optical head 100. The electronic apparatus 1 is configured to provide the incident reflected light to the camera 200 of the portable terminal 2. In this case, the output light 700 may involve a specific pattern, and the portable terminal 2 may collect three-dimensional (3D) information in which curvature of a skin is three-dimensionally rendered based on the specific pattern involved in the light 700. The portable terminal 2 may be configured to measure healing of a wound, and the length, width and height of a pigmented mole such as a pimple, a mole, etc. through a specific pattern, analyze measured 3D information, and provide more correctly analyzed diagnosis information to a user. In this case, the pattern involved in the light 700 may be formed using an infrared ray (IR) invisible to a user.

Figure 7:
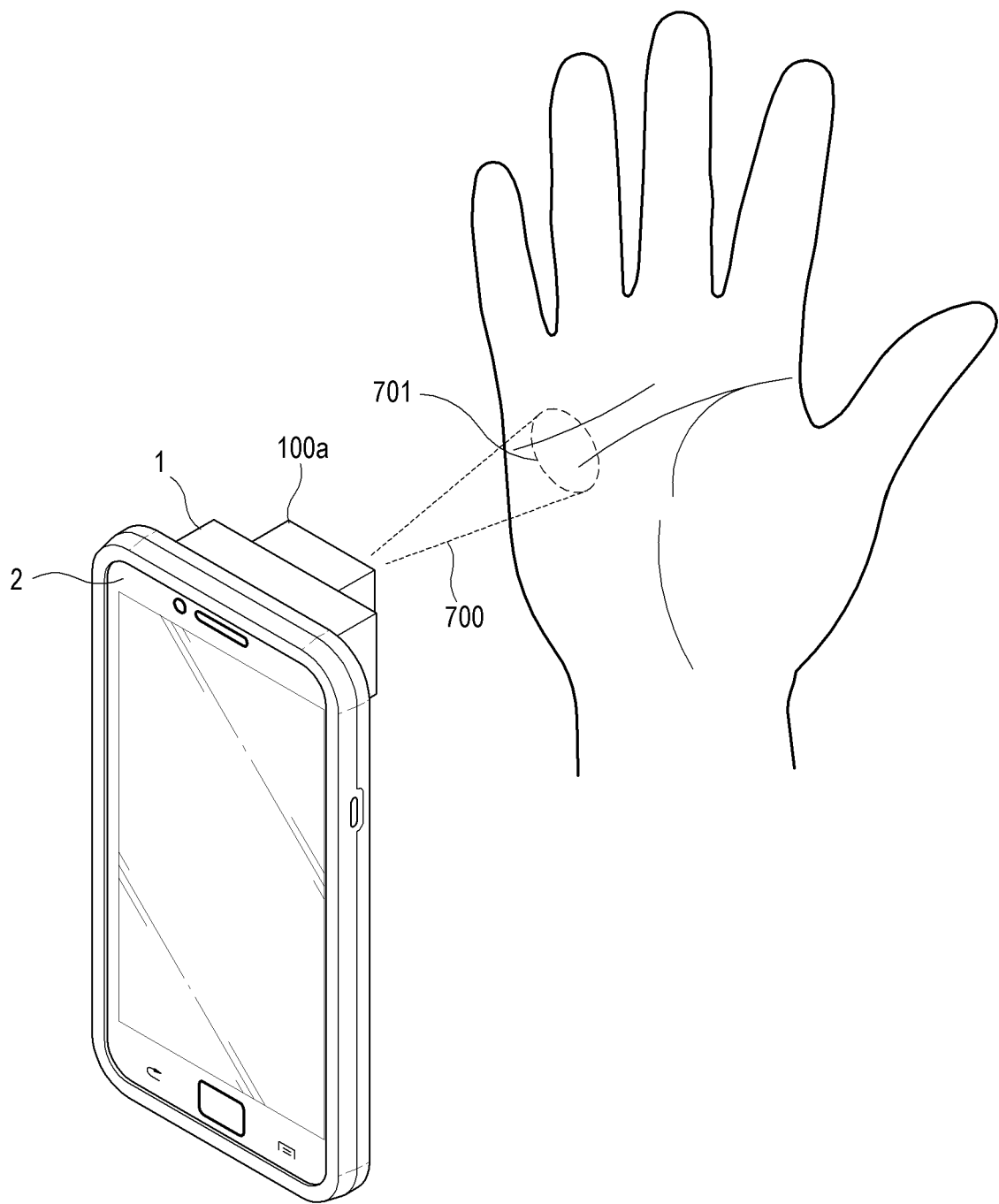
FIG. 7 shows an example of using a portable terminal, an electronic apparatus and an optical head according to one embodiment of the present invention.
Figure 8:
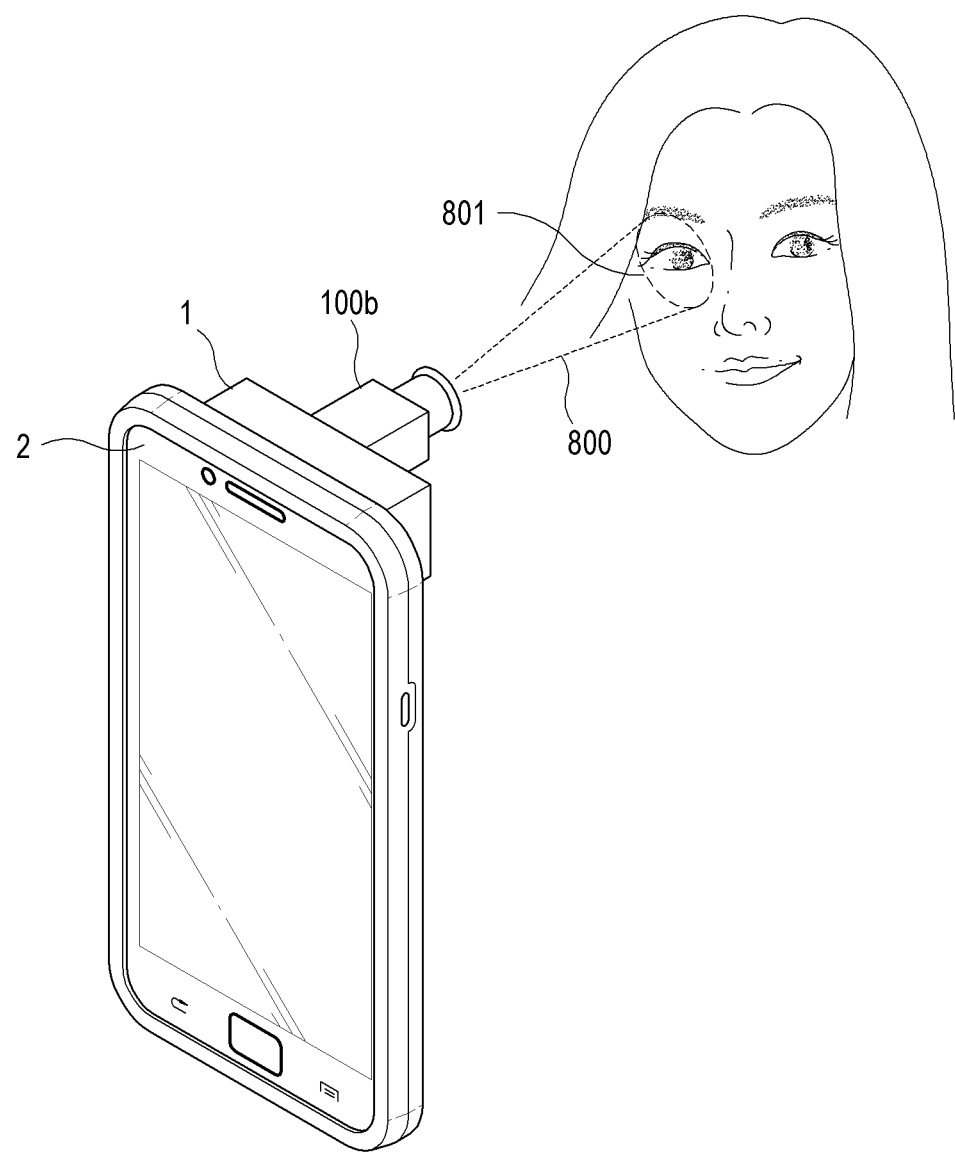
FIG. 8 shows an example of using a portable terminal, an electronic apparatus and an optical head according to one embodiment of the present invention.
Figure 9:
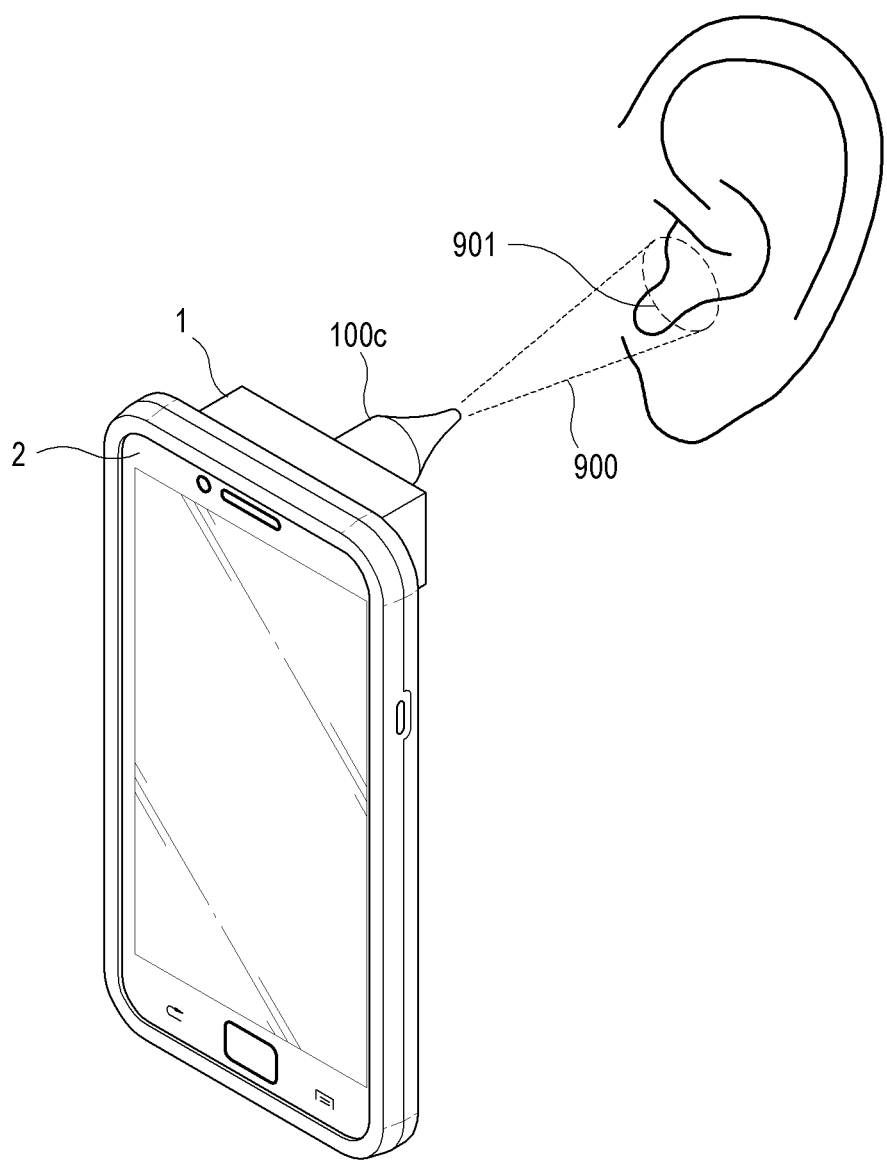
FIG. 9 shows an example of using a portable terminal, an electronic apparatus and an optical head according to one embodiment of the present invention.

FIGS. 7, 8 and 9 show examples of using a portable terminal, an electronic apparatus and an optical head according to one embodiment of the present invention.

The plurality of optical heads 100 is selected based on a user's body part desired to be captured, and mounted to the electronic apparatus 1.

Referring to FIG. 7, the optical head 100 corresponding to the dermatoscope may be mounted to the electronic apparatus 1 so as to capture an image of a user's skin part 701 of a user skin. The light 700 generated and output from the electronic apparatus 1 is emitted to the user's skin part 701 through the optical head 100, and light reflected from the skin part 701 returns to the electronic apparatus 1 through the optical head 100. The electronic apparatus 1 is configured to provide the light received through the mounted optical head 100 to the camera 200 of the portable terminal 2.

The portable terminal 2 is configured to provide an image obtained by capturing an image of a user's skin part 701 to a user through the display 101. The optical head 100 corresponding to the dermatoscope is in contact with a user's skin part 701, and captures an enlarged image of the contact skin part 701 without distortion.

Referring to FIG. 8, the optical head 100 corresponding to the ophthalmoscope may be mounted to the electronic apparatus 1 so as to capture an image of a user's eye 801.

The optical head 100*b* corresponding to the ophthalmoscope is configured to examine a user's vitreous body, retina, choroid membrane, optic disk or the like eye ground. By examining the eye ground, it is possible to diagnose glaucoma, macular degeneration, detached retina or the like disease.

To this end, the optical head 100*b* corresponding to the ophthalmoscope emits light 800 generated in the electronic apparatus 1 to a user's eye ground, and provides the reflected light to the electronic apparatus 1. The electronic apparatus 1 is configured to provide light received through the optical head 100*b* to the camera 200 of the portable terminal 2.

Further, the camera 200 is configured to convert an image of a user's eye 801 based on the received light into an electric signal, and the display 101 is configured to display the image of the eye 801 based on the electric signal. In this case, a guide image may be provided to easily capture a lesion in the retina.

Referring to FIG. 9, the optical head 100*c* corresponding to the otoscope is mounted to the electronic apparatus 1 so as to capture an image of a user's inner ear 901.

The optical head 100*c* corresponding to the otoscope may be configured as a conical metal cylinder to push earwax and an ear tuft aside and be inserted in an external auditory meatus to examine the external auditory meatus, a middle ear, and an eardrum. The optical head 100*c* may be variously configured to have a diameter of 2~7 mm at a front opening portion.

Light 900 generated and output from the electronic apparatus 1 is emitted to a user's inner ear 901 through the front opening portion of the optical head 100*c*, and reflected light returns to the electronic apparatus 1 through the optical head 100*c*. The electronic apparatus 1 is configured to provide incident light to the camera 200 of the portable terminal 2.

Further, the camera 200 is configured to convert an image of a user's inner ear 901 based on the received light into an electric signal, and the display 101 is configured to display the image of the inner ear 901 based on the electric signal. As described above, the optical head 100 may include a sensing section such as an optical temperature sensor or the like. The portable terminal 2 may use a captured image and a body temperature measured by the sensing section of the optical head 100 to make a diagnosis of otitis media or the like disease of which diagnosis is based on measured temperature.

Figure 10:
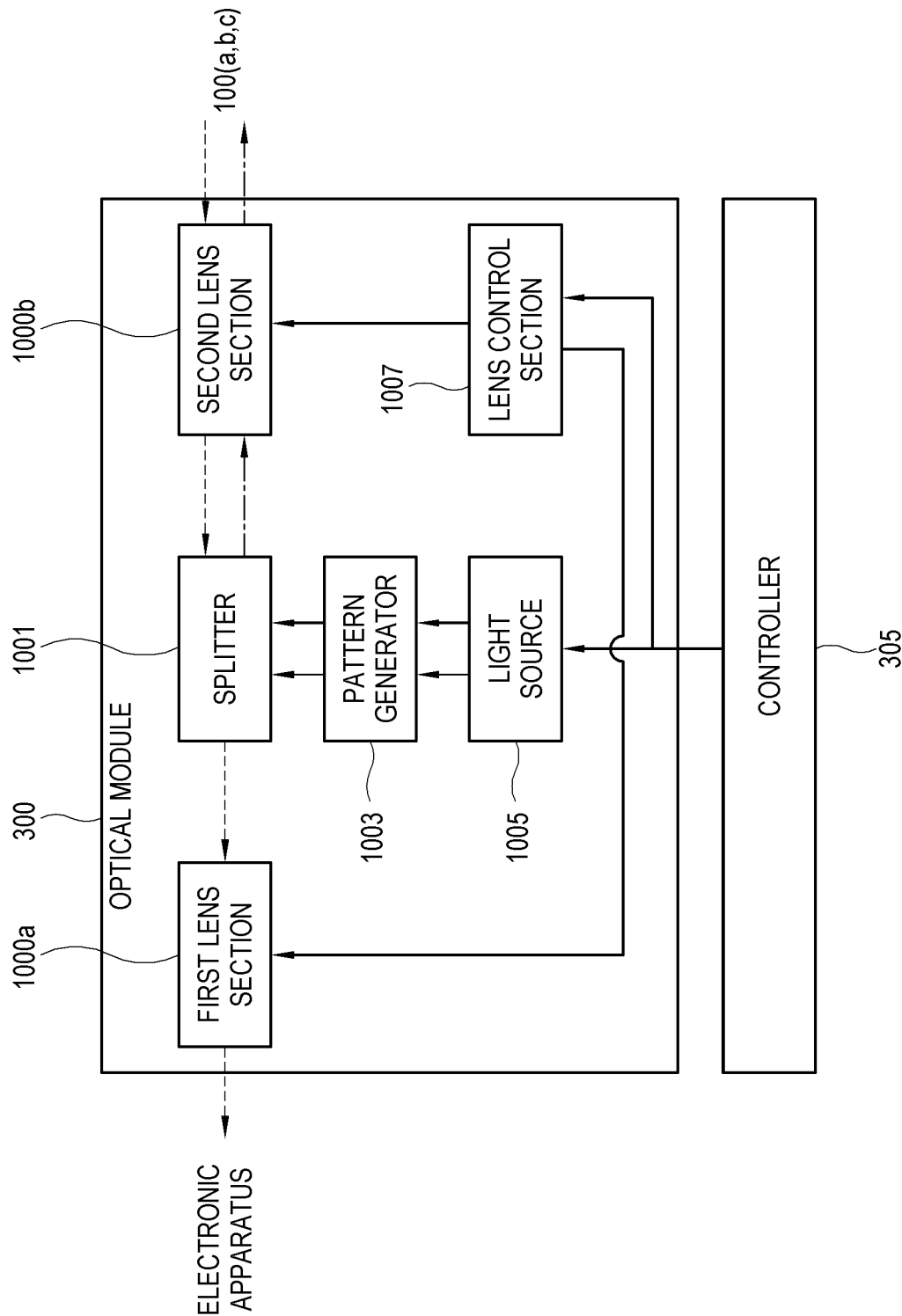
FIG. 10 is a block diagram of an optical module in an electronic apparatus according to one embodiment of the present invention.

FIG. 10 is a block diagram of an optical module in an electronic apparatus according to one embodiment of the present invention.

The optical module 300 serves to transmit light reflected from a user's body to the portable terminal 2, and is configured to generate light based on a control signal received from the portable terminal 2 and output the light through the mounted optical head 100.

Referring to FIG. 10, the optical module 300 may include first and second lens sections 1000*a* and 1000*b*, a splitter 1001, a pattern generator 1003, a light source 1005 and a lens control section 1007.

To observe a user's body part, the first and second lens sections 1000*a* and 1000*b* may include a plurality of lenses such as an ocular lens for receiving light reflected from a user's body and transmitting the light to the portable terminal 2, an objective lens for focusing an image of an object, and a relay lens interposed between the ocular lens and the objective lens and inverts an inverted image on the objective lens. The optical module 300 may include at least one lens sections 1000*a* and 1000*b*, and the illustrated first and second lens sections 1000*a* and 1000*b* are not construed as limiting the optical module 300 of the present invention. That is, the drawings and the foregoing descriptions are merely an example, and do no limit the number and characteristics of lenses included in the optical module 300.

The lens control section 1007 is configured to control the focal length of the lenses in the lens sections 1000*a* and 1000*b*. More specifically, to control the focal length at which an image is focused based on the light from the optical head 100 in accordance with the mounted optical head 100, it is possible to adjust a distance between the lenses, and the size, the thickness, the curvature, etc. of lenses. To this end, each of the lens sections 1000*a* and 1000*b* includes a plurality of lenses different in size, thickness and curvature, and the position of the lenses are adjustable under control of the lens control section 1007.

The light source 1005 is configured to generate and output light to a user's body part. The light source 1005 may include a light emitting diode (LED) for emitting light when power is supplied.

The splitter 1001 reflects light generated by the light source 1005 toward the optical head 100 through the second lens section 1000*b*, and transmits light received from the optical head 100 to the portable terminal 2 through the first lens section 1000*a*.

The pattern generator 1003 generates a pattern and applies the pattern to the light generated in the light source 1005. For instance, when the light source 1005 generates light to be emitted to a skin, the pattern generator 103 makes various patterns such as an orthogonal grid pattern and the like so that a characteristic size of a lesion, a mole, a pimple, a wound, etc. on a user's skin. Further, it is possible to obtain 3D information of an image captured using this pattern. The pattern generator is configured to store various patterns and apply the pattern, which is selected in response to a control signal received from the portable terminal 2, to the output light.

Figure 11:
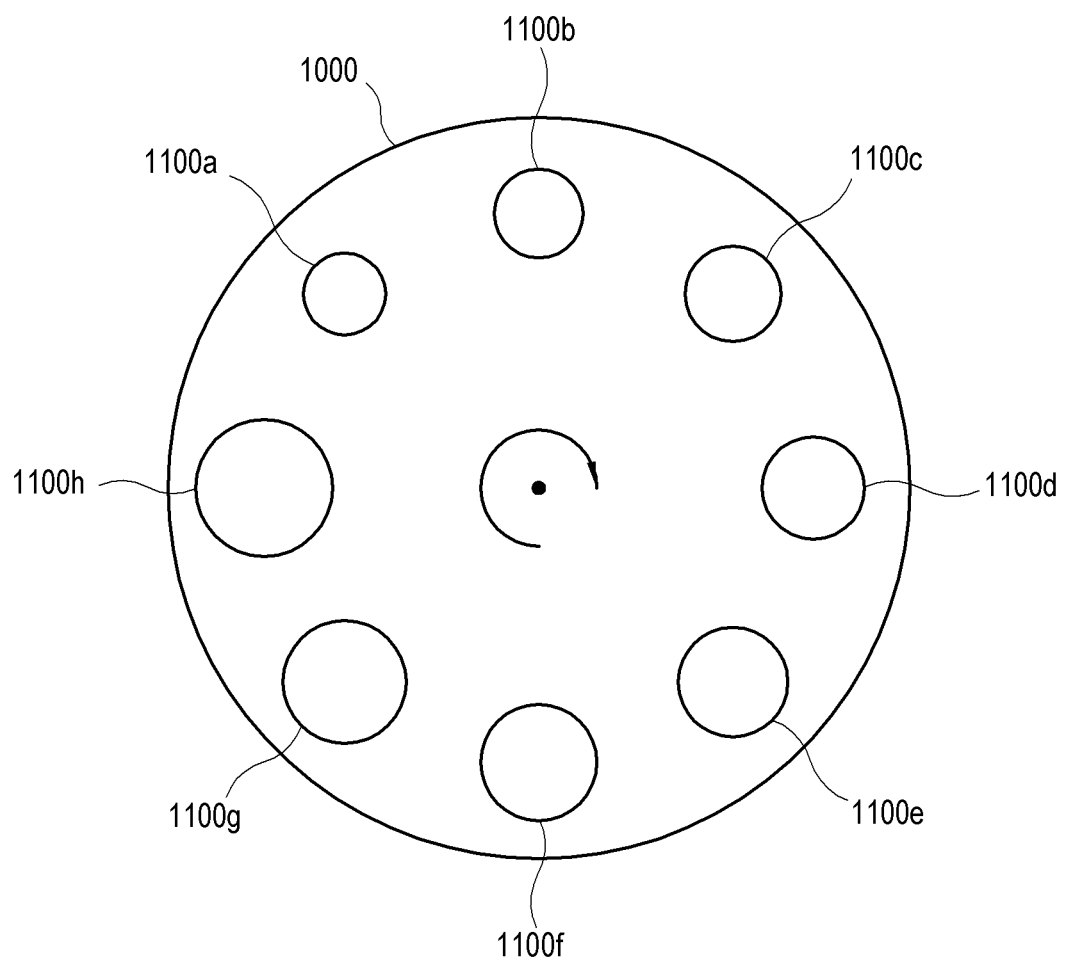
FIG. 11 shows an example of a lens section according to one embodiment of the present invention.

FIG. 11 shows an example of a lens section according to one embodiment of the present invention.

As described above, the optical module 300 may include the first and second lens sections 1000*a* and 1000*b*. The lens used in each of the lens sections 1000*a* and 1000*b* can be changed in size, thickness and curvature under control of the lens control section 1007.

The plurality of optical heads 100 are respectively used for different purposes, and employ the lenses different in size corresponding to different purposes. Thus, there is a need of adjusting the focal lengths of the light provided by the optical module 300 and the light incident to the optical module 300 through the optical head 100 in accordance with the mounted optical head 100 or in response to a user's selection To adjust the focal length, the electronic apparatus 1 may be configured to automatically adjust a focus in response to a control signal received from the portable terminal 2 like that of the related art. Further, the lens used in each of the lens sections 1000*a* and 1000*b* is adjustable in size, thickness and curvature. To this end, each of the lens sections 1000*a* and 1000*b* may include a plurality of lenses 1100*a*~1100*h* different in size.

Referring to FIG. 11, the plurality of lenses 1100*a*~1100*h* is provided in a spinning plate. The lens control section 1007 may be configured to turn the spinning plate under control of the controller 305 so that the lens 1100*a*~1100*h* of a necessary size can be mounted. FIG. 11 illustrates that the spinning plate includes the plurality of lenses 1100*a*~1100*h* different in size. Alternatively, the spinning plate may include a plurality of lenses different in thickness and curvature as well as size.

Figure 12:
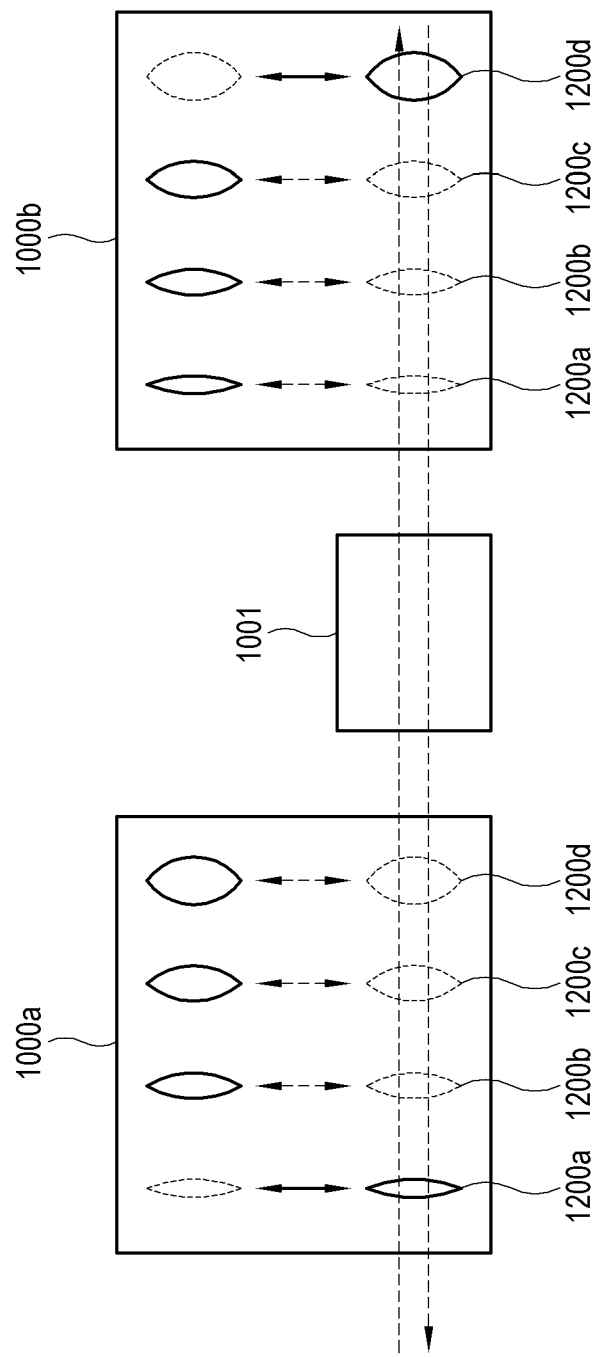
FIG. 12 shows an example of a lens section according to another embodiment of the present invention.

FIG. 12 shows an example of a lens section according to another embodiment of the present invention.

The lens sections 1000*a* and 1000*b* may be respectively configured to use a plurality of lenses 1200*a*~*d* and 1201*a*~*d* different in thickness as well as size. The thickness of the lenses 1200*a*~*d* and 1201*a*~*d* also has an effect on changing the focal length. As described above, the plurality of lenses 1200*a*~*d* and 1201*a*~*d* different in thickness from one another may be applied to the spinning plate shown in FIG. 11.

FIG. 12 illustrates an example that the plurality of lenses 1200*a*~*d* and 1201*a*~*d* different in thickness from one another moves to an optical path under control of the lens control section 1007. Unlike the spinning plate of FIG. 11, each of the lens sections 1000*a* and 1000*b* in this embodiment may be configured to employ at least one among the plurality of lenses 1200*a*~*d* and 1201*a*~*d* different in thickness from one another. FIG. 12 shows that the plurality of lenses 1200*a*~*d* and 1201*a*~*d* are all provided as convex lenses, but not limited thereto. Alternatively, the plurality of lenses 1200*a*~*d* and 1201*a*~*d* may include various types of lenses such as a convex lens, a concave lens and a combination lens, etc.

Figure 13:
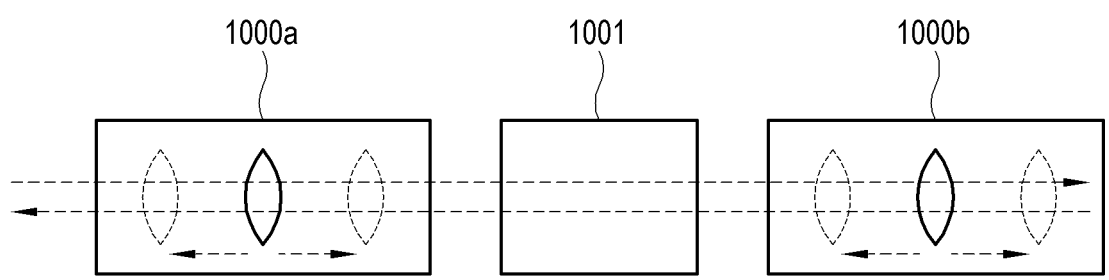
FIG. 13 shows an example of a lens section according to another embodiment of the present invention.

FIG. 13 shows an example of a lens section according to another embodiment of the present invention.

Each of the lens sections 1000*a* and 1000*b* includes the plurality of lenses 1100*a*~*h*, 1200*a*~*d* and 1201*a*~*d* different in thickness and size from one another, and the lenses are used as necessary to thereby adjust the focal lengths of the lens sections 1000*a* and 1000*b*. Further, the lens sections 1000*a* and 1000*b* are configured to adjust the focal length by controlling a distance between the lens used, i.e. aligned with the optical path.

As the plurality of lenses move away from or close to each other, a focus for an image is adjusted. Thus, to capture an image of a user's body part based on the mounted optical head 100, the used lens may be changed in size and thickness as described above, and the position of the lens may be controlled to adjust the focus as described in this embodiment. The position of the lens may be changed by various publicly known techniques.

FIGS. 11, 12 and 13 are merely for describing that the electronic apparatus 1 according to one embodiment of the present invention can use a combination of different lenses 1100a~h, 1200a~d and 1201a~d. Alternatively, the electronic apparatus 1 may employ various methods for adjusting the focal length of the emitted, reflected or incident light.

Figure 14:
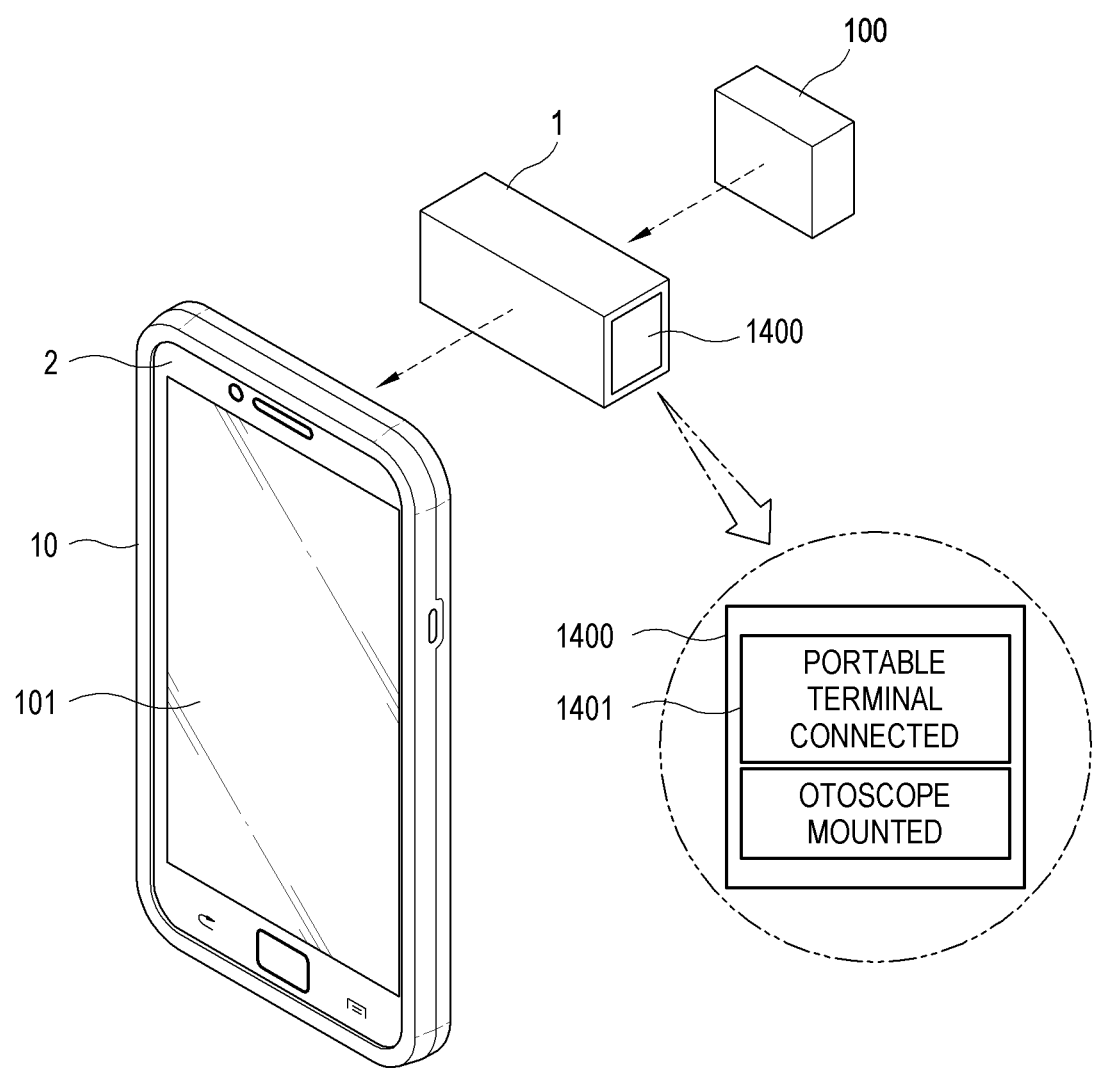
FIG. 14 shows an example of an electronic apparatus according to one embodiment of the present invention.

FIG. 14 shows an example of an electronic apparatus according to one embodiment of the present invention.

The electronic apparatus 1 may include a display 1400 for displaying a current state 1401 of the electronic apparatus 1. The current state 1401 refers to information about whether the electronic apparatus 1 is connected to the portable terminal 2, what optical head 100 is mounted, etc., and the display 1400 may display the current state 1401 of the electronic apparatus 1 by a text or an image.

According to another embodiment, the display 1400 may be configured to display information about a pattern applied to light emitted to a user's body part, information about whether the lens focuses an image, information about the lens used in the lens sections 1000a and 1000b, and the like information about functions supported by the electronic apparatus 1. Since the information is provided through the display 14000 of the electronic apparatus 1, it is more convenient for a user to use the electronic apparatus 1.

Figure 15:
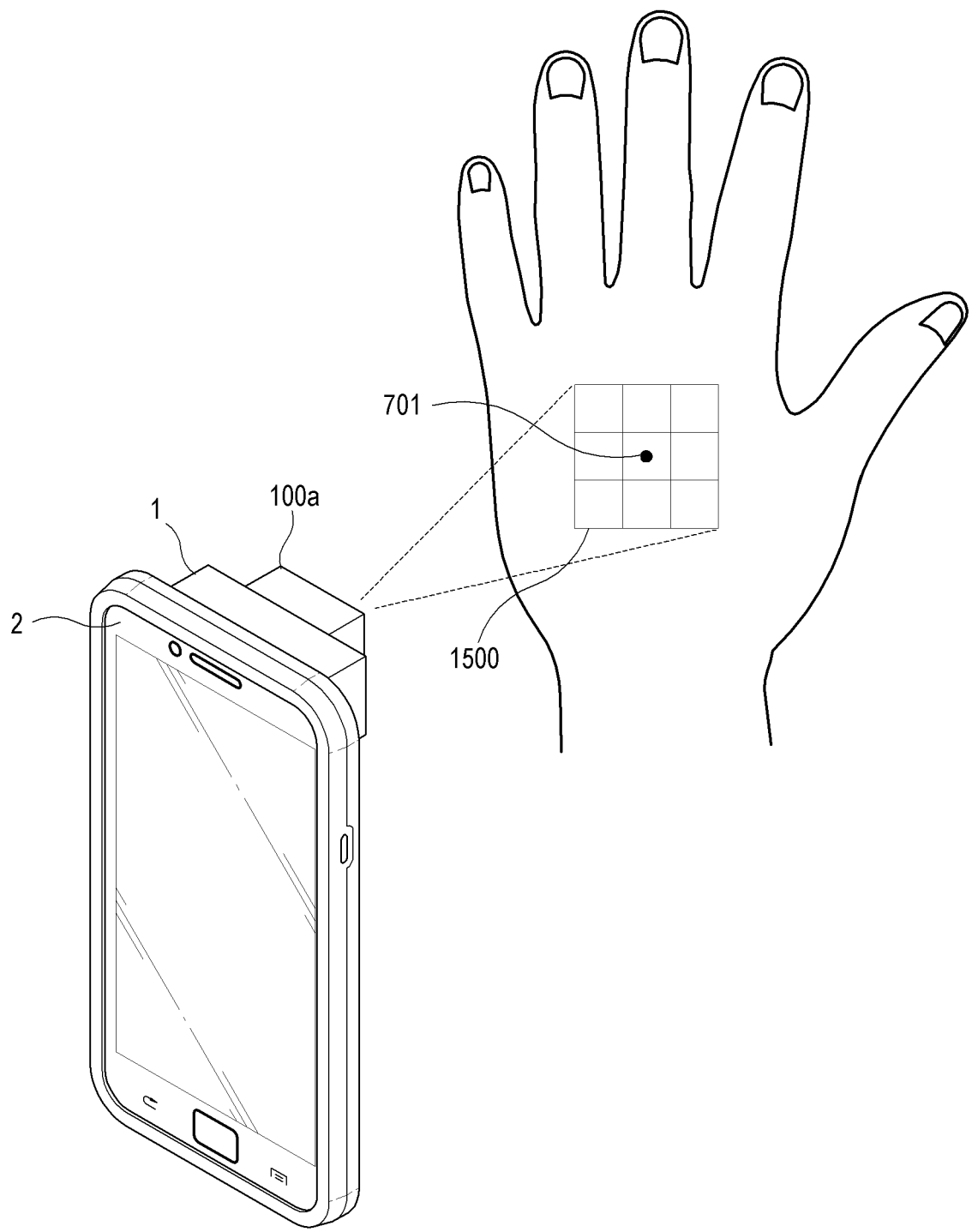
FIG. 15 shows an example of using a portable terminal, an electronic apparatus and an optical head according to one embodiment of the present invention.
Figure 16:
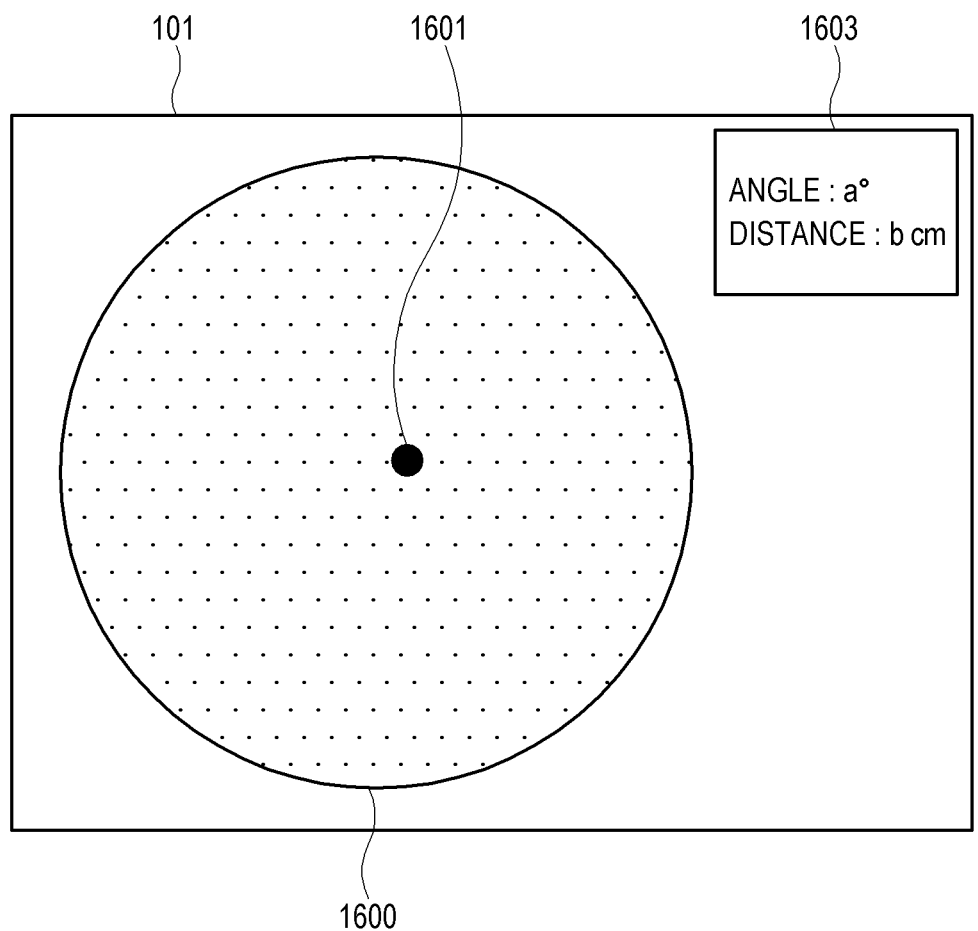
FIG. 16 shows an example of using a portable terminal, an electronic apparatus and an optical head according to one embodiment of the present invention.
Figure 17:
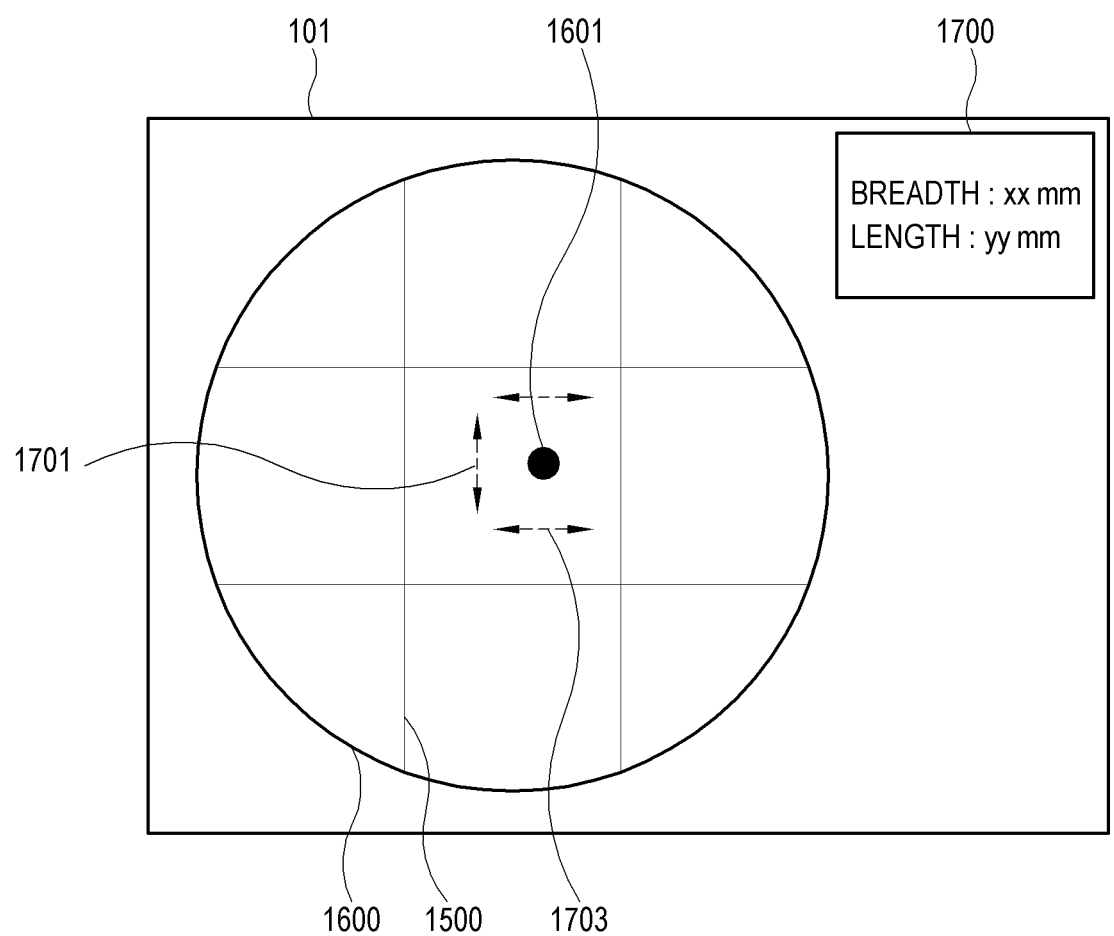
FIG. 17 shows an example of using a portable terminal, an electronic apparatus and an optical head according to one embodiment of the present invention.

FIGS. 15, 16 and 17 show examples of using a portable terminal, an electronic apparatus and an optical head according to one embodiment of the present invention.

Referring to FIG. 15, the portable terminal 2, the electronic apparatus 1 and the optical head 100 are combined to capture an image of a user's skin. A user mounts the optical head 100 corresponding to the dermatoscope for capturing a skin to the electronic apparatus 1, and the electronic apparatus 1 is coupled to the case 10 of the portable terminal 2 and operates by receiving power from the portable terminal 2.

Then, a user controls the portable terminal 2 to capture an image of a user's skin part, so that light reflected from the skin part can be transmitted to the camera 200 of the portable terminal 2 through the optical head 100 and the electronic apparatus 1. The camera 200 converts the indicate light into an image based on an electric signal, and the display 101 provides the image to a user.

A mole 701 on a user's skin or a lesion detected in a skin part may be an initial symptom of skin cancer. To determine a shape of the mole 701, measure the size of the mole 701, and analyze whether the measured mole 701 is changed in size or shape, a user may take an image. To more accurately determine the shape and size of the mole 701, the electronic apparatus 1 may further include the pattern generator 1003 for generating a pattern 1500, and determine the size of the mole by comparing the generated pattern and the mole 701. Further, 3D information may be obtained based on the generated and applied pattern.

Referring to FIG. 16, the captured skin 1600 is displayed through the display 101.

When a user takes an image of the skin 1600 to enlarge and capture the mole 701 in a hand, the controller 400 of the portable terminal 2 controls the display 101 to display information 1603 about an angle at which the portable terminal 2 is positioned to capture an image of a user's body part and a distance from the user's body part, and a user's skin image 1600 including the mole 1601 on the user's hand. Further, the display 101 may display a 3D image, which includes height of a mole, a skin lesion, a wound or the like, based on the previously obtained 3D information.

The angle of the portable terminal 2 and the distance from a user's body part may be used to capture an image of a user's body part at the same position in the future, and may be provided as the guide information to the user.

FIG. 17 illustrates that the pattern 1500 generated by the pattern generator 1003 is displayed together with a user's skin 1600 through the display 101.

When a user controls the portable terminal 2 to accurately measure the size of the mole 701 on the skin, the portable terminal 2 transmits a control signal caused by a user's control to the electronic apparatus 1 through the communicator 401, and the pattern generator 1003 of the electronic apparatus 1 generates the pattern 1500 applies the pattern 1500 to the output light based on the control signal. A user compares the pattern 1500 displayed through the display 101 and the mole 1601, thereby directly measuring the size of the mole 1601.

According to another embodiment, the controller 400 of the portable terminal 2 may be configured to directly use the pattern 1500 in measuring a breadth 1703 and a length 1701 of the mole 1601 and the height based on the 3D information. Then, the controller 400 may provide information 1700 about the measured size of the mole to a user through the display 101.

Figure 18:
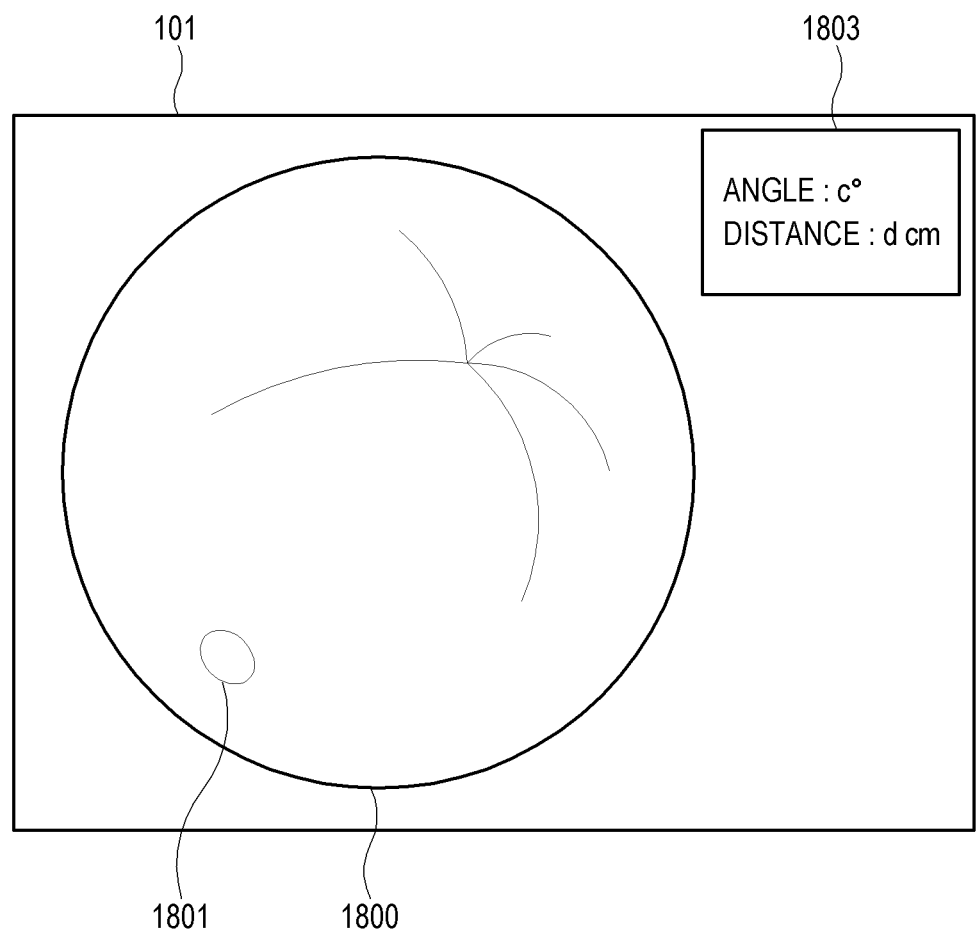
FIG. 18 shows an example of capturing an eyeball and providing an image and information of the captured eyeball according to one embodiment of the present invention.
Figure 19:
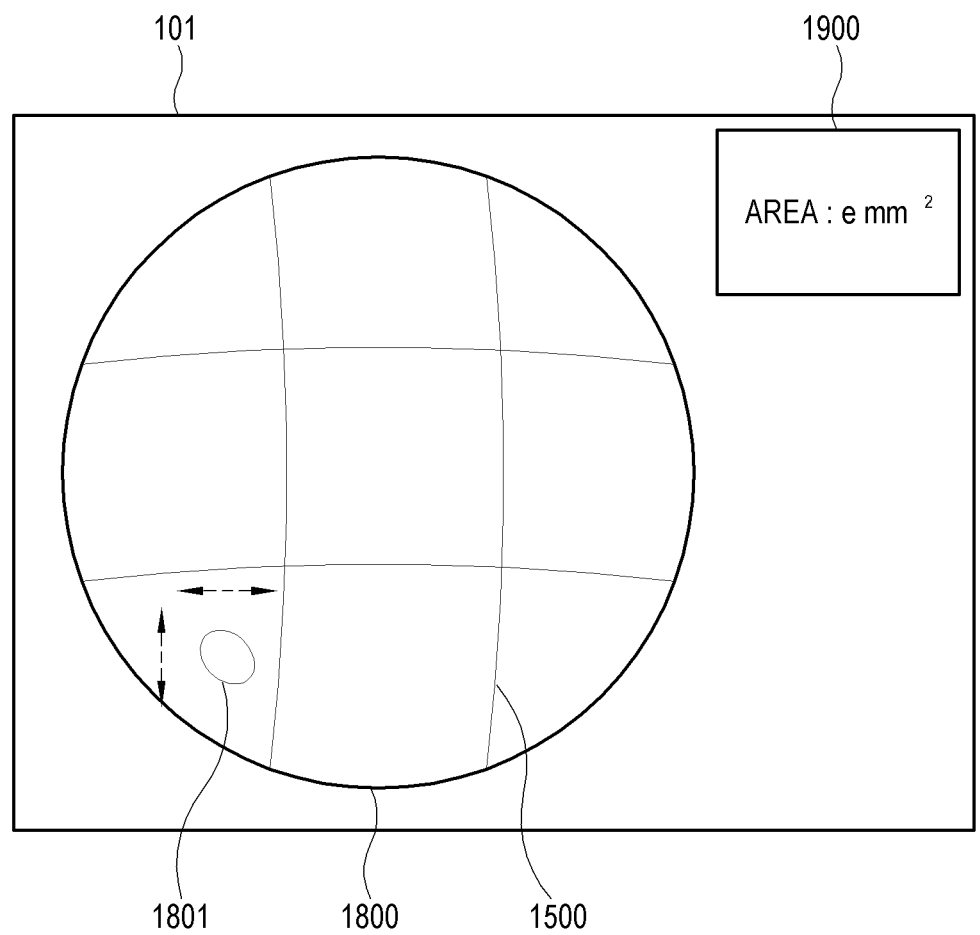
FIG. 19 shows an example of capturing an eyeball and providing an image and information of the captured eyeball according to one embodiment of the present invention.

FIGS. 18 and 19 show an example of capturing an eyeball and providing an image and information of the captured eyeball according to one embodiment of the present invention.

The electronic apparatus 1 emits light to the eye ground through an opening of the optical head 100 corresponding to the mounted ophthalmoscope, and provides light reflected from the eye ground and incident through the optical head 100 to the camera 200 of the portable terminal 2. The camera 200 generates an image of a vitreous body, an optic disk, a retina, a choroid and a blood vessel in the eyeball based on the received light, and the display 101 provides the generated image.

FIG. 18 shows an example that the portable terminal 2 employs the optical head 100 corresponding to the ophthalmoscope mounted to the electronic apparatus 1 and provides a captured image 1800 and information 1803 through the display 101.

The image 1800 of the eyeball includes a vitreous body, a nerve, a blood vessel, etc. When there is an opaque point 1801 in the eyeball, it may be an initial symptom of a disease in the eyeball and there is a need of analyzing the shape and size of the opaque point 1801. Further, the eyeball is captured leaving a time lag to thereby analyze whether the opaque point 1801 gradually becomes bigger.

The controller 400 of the portable terminal 2 controls the display 101 to display information 1803 about an angle at which the portable terminal 2 is positioned to capture an image of a user's body part and a distance from the user's body part, and a user's eyeball image 1800 including the opaque point 1801 in the user's eyeball.

Further, when the pattern 1500 is applied from the pattern generator 1003, a user can directly determine the size of the opaque point 1801 in the eyeball on the basis of the pattern 1500 applied to the image, and the controller 400 can directly analyze the area based on the pattern 1500.

The controller 400 directly analyzes the area of the opaque point 1801 in the eyeball, and then provides analysis result information 1900 to the display 101.

Figure 20:
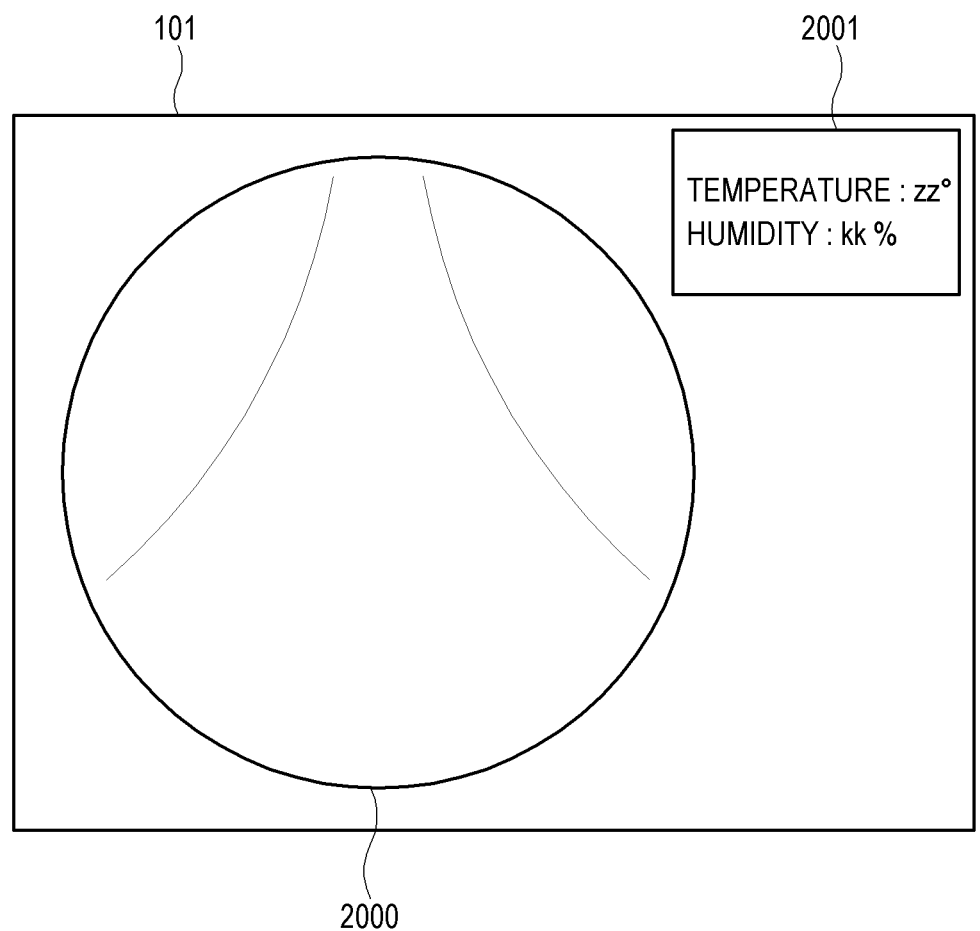
FIG. 20 shows an example of an inner ear and providing an image and information of the inner ear according to one embodiment of the present invention.

FIG. 20 shows an example of capturing an inner ear and providing an image and information of the captured inner ear according to one embodiment of the present invention.

When the optical head 100c corresponding to the otoscope is mounted to the electronic apparatus 1, and a user inserts an opening of the optical head 100c into the inner ear and controls the portable terminal 2 to take an image of the inner ear, the electronic apparatus 1 emits light to the inner ear through the front opening portion of the optical head 100c on the basis of a control signal transmitted from the portable terminal 2, and transmits light reflected from the inner ear and incident through the optical head 100c to the camera 200 of the portable terminal 2. The camera 200 converts the transmitted light into an image, and the display 101 provides the image of inner ear to a user.

As described above, the optical head 100c may further include the sensing section 503. The sensing section 503 may measure a biometric signal such as brainwaves in the inner ear, or sense a user's body temperature and humidity in the inner ear, thereby providing the sensed information to the electronic apparatus 1. The electronic apparatus 1 transmits the received information to the portable terminal so that the received information can be provided to a user. The portable terminal 2 may provide information 2001 about the sensed temperature and humidity to a user through the display 101.

Figure 21:
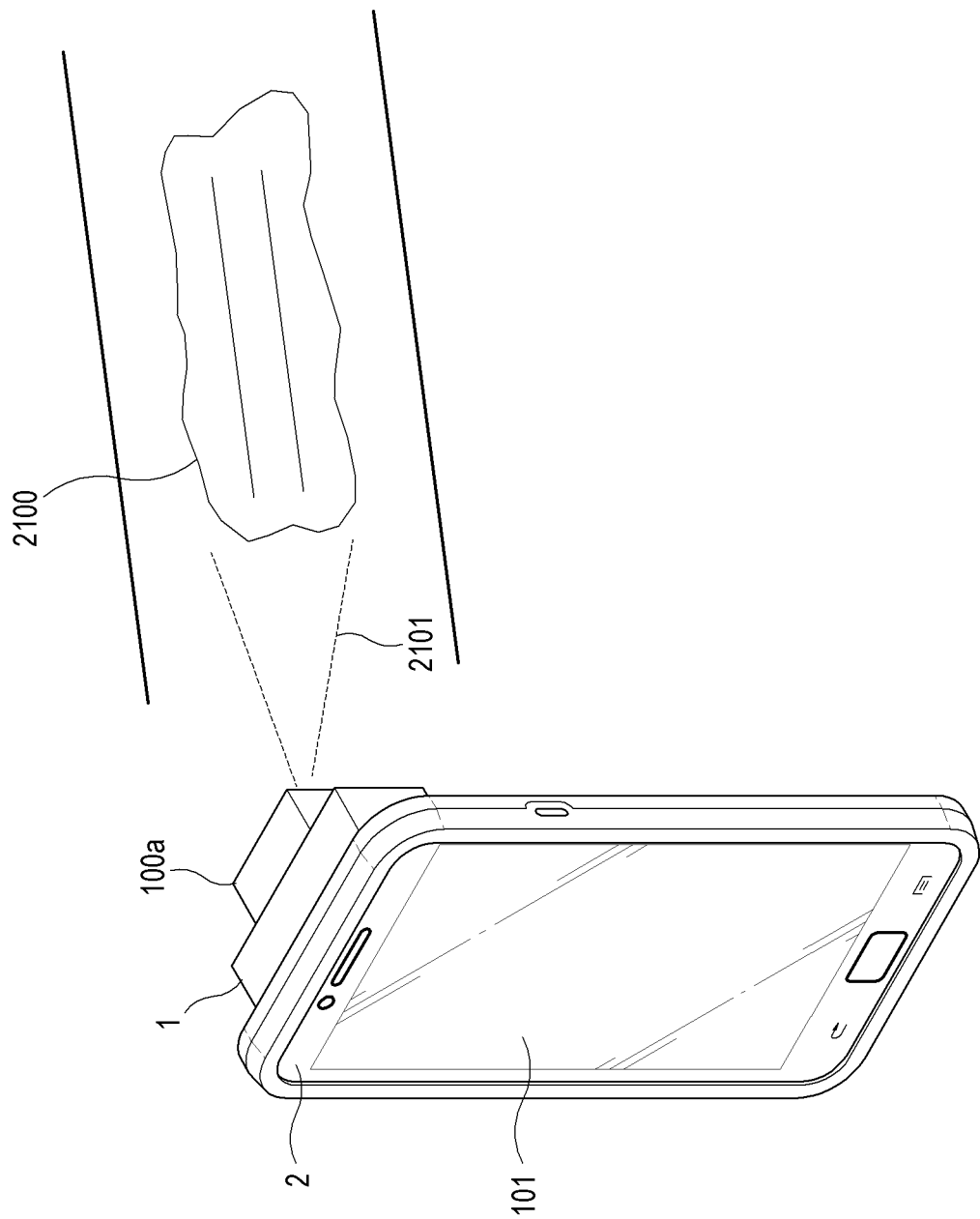
FIG. 21 shows an example of capturing a skin wound of a user according to one embodiment of the present invention.

FIG. 21 shows an example of capturing a skin wound of a user according to one embodiment of the present invention.

A user may take an image of a skin to analyze a wound recovery process with regard to a wound on the skin as well as a mole or a skin lesion. Referring to FIG. 21, the electronic apparatus 1 coupled to the portable terminal 2 is mounted with the optical head 100a corresponding to the dermatoscope, emits light 2101 to capture an image of a user's skin wound 2100, and generates an image based on the reflected light.

Figure 22:
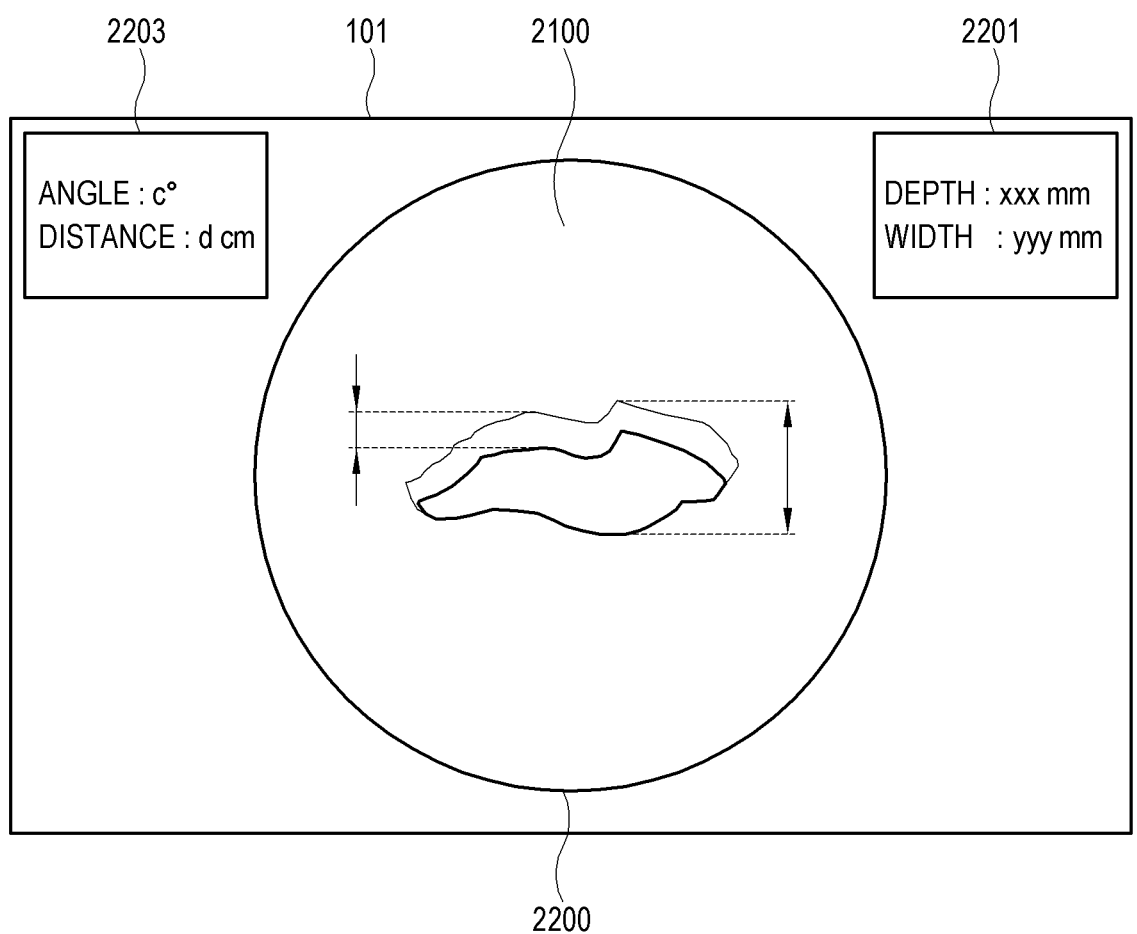
FIG. 22 shows an example of displaying a captured skin wound of a user according to one embodiment of the present invention.

FIG. 22 shows an example of displaying a captured skin wound of a user according to one embodiment of the present invention.

The light source 1005 of the electronic apparatus 1 may be configured to output a laser beam for analyzing a user's skin wound 2100 to the wound 2100, and receive the laser beam reflected from the wound 2100. The electronic apparatus 1 may generate information about the wound 2100 based on the received laser beam, and transmit the generated information to the portable terminal 2 through the communicator 303. The controller 400 of the portable terminal 2 may be configured to analyze the depth and width of the wound 2100 based on the information about the wound 2100 received from the electronic apparatus 1.

Further, the controller 400 of the portable terminal 2 may control the display 101 to provide an image 2200 of a user's skin including the wound 2100, information 2201 about the analyzed depth and width of the wound 2100, and information 2203 about an angle and distance from a user's body part when the portable terminal 2 takes an image of a user's skin.

FIGS. 23, 24, 25 and 26 shows examples of a user interface (UI) provided through a display according to one embodiment of the present invention.

Before a user measures his/her body part, the portable terminal 2 may provide guide information through the UI for performing related functions of the portable terminal 2.

The guide information includes the kind of optical head 100 to be mounted corresponding to a body part desired to be captured, an action to be made by a user, and the like information to be referenced by a user to capture a body part.

Figure 23:
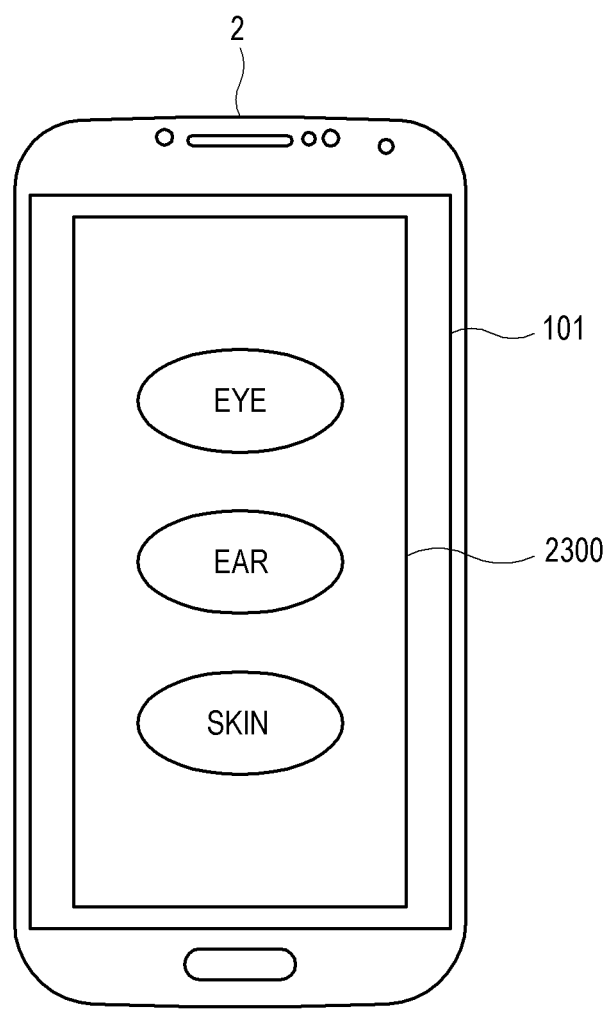
FIG. 23 shows an example of a user interface (UI) provided through a display according to one embodiment of the present invention.
Figure 24:
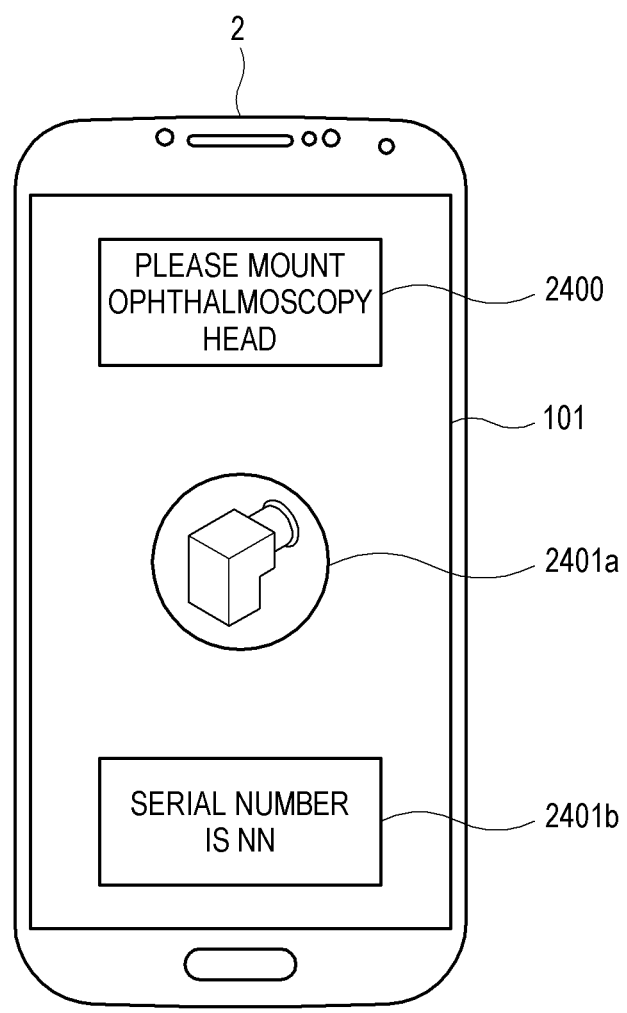
FIG. 24 shows an example of a UI provided through a display according to one embodiment of the present invention.

Referring to FIG. 23, a UI is provided including a menu item 2300 corresponding to a body part desired to be captured by a user. A user selects one menu item 2300 corresponding to an eye, an ear or a skin desired to be examined among the displayed menu items 2300, and moves to the next process.

The illustrated UI is merely an example given for description. To examine a body part, more various UIs selectable by a user may be provided to the user. Alternatively, a user may select a suspicion of a cataract with vision loss in a case of examining the eye, examination whether a skin wood heals over in a case of examining the skin, and the like more detailed item to be diagnosed through the UI.

When a user selects an eye to be captured in the UI of FIG. 23, the display 101 may display a UI as shown in FIG. including various pieces of guide information such as the kind 2400 of optical head 100 needed to be mounted by a user to the electronic apparatus 1, an appearance 2401a of the optical head 100, a serial number 2401b, etc.

The illustrated guide information is merely an example. More specifically, there are various pieces of information for guiding a user.

Figure 25:
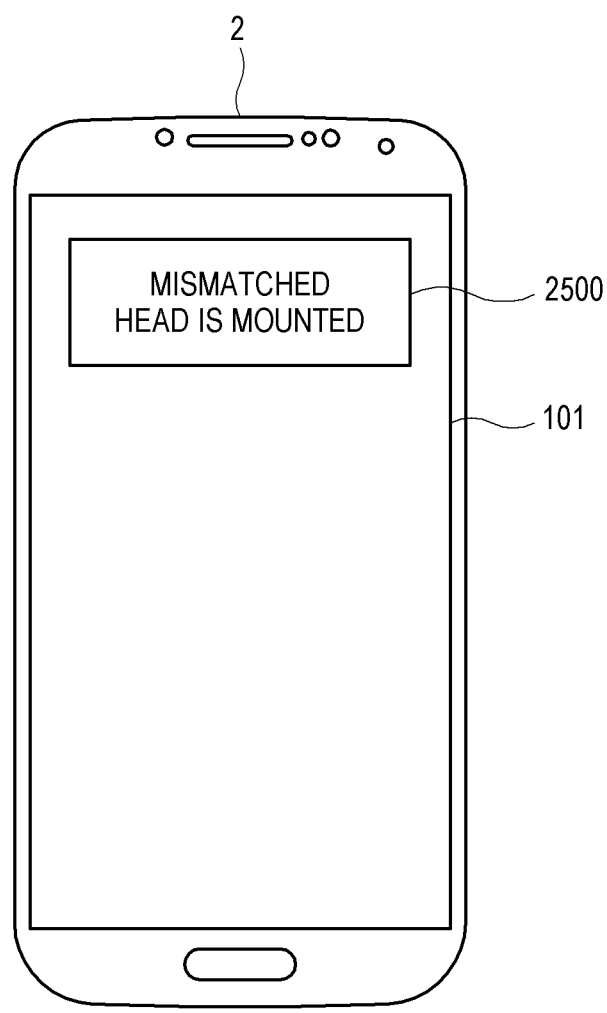
FIG. 25 shows an example of a UI provided through a display according to one embodiment of the present invention.

FIG. 25 shows a UI provided when a user mounts the optical head 100 mismatching with a body part desired to be examined. Each optical head 100 is storing the identification information, and it is thus possible to determine based on the identification information what kind of optical head 100 is mounted to the electronic apparatus 1 by a user. The controller 400 of the portable terminal 2 compares an item selected by a user to capture a body part with the identification information of the mounted optical head 100, and controls the display 101 to provide a UI including a guide 2500 for informing a user of a mismatch when the mounted optical head 100 mismatches with the optical head 100 corresponding to the item selected by the user.

According to another embodiment, when the mounted optical head 100 mismatches with the optical head 100 corresponding to the selection, the controller 400 of the portable terminal 2 may control the display 101 to provide guide information once again so that the optical head 100 corresponding to the selection can be correctly mounted.

According to still another embodiment, when the mounted optical head 100 mismatches with the optical head 100 corresponding to a user's selection, the controller 400 of the portable terminal 2 may ask a user about whether s/he will change the selection of his/her body part to be examined.

Figure 26:
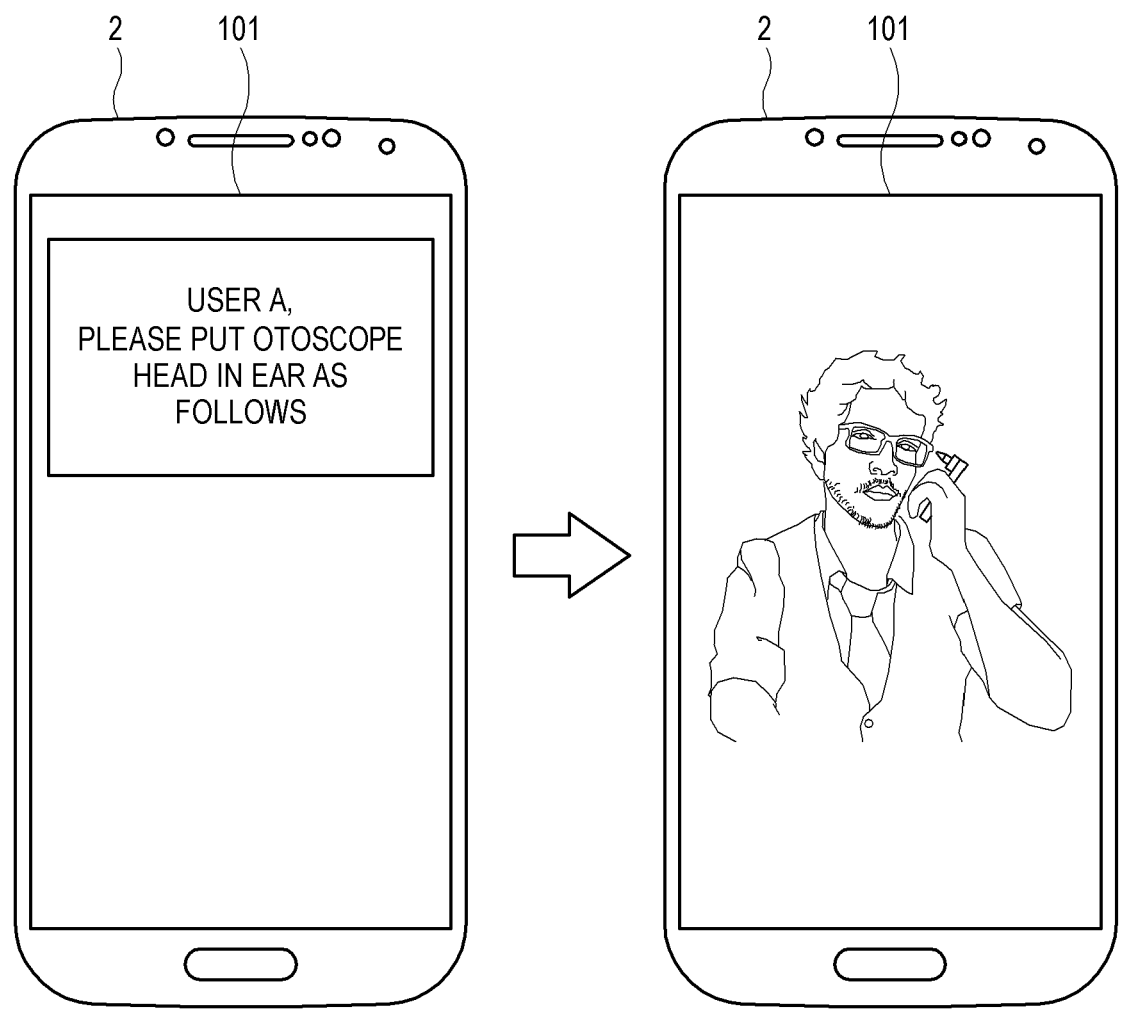
FIG. 26 shows an example of a UI provided through a display according to one embodiment of the present invention.

Referring to FIG. 26, a user is guided to capture an image of an ear through a mounted optical head.

A user takes an image of his/her body part along with guide information given in the form of a photograph or other pictures on the display 101, and previously determines whether there is a health problem based on the captured image or transmits the captured image to the outside for making a diagnosis.

The identification information of the optical head 100 may include not only information about the kind of optical head 100, but also unique information such as a serial number of the optical head 100. Thus, when used optical heads 100 are different according to users with regard to the same kind of optical head 100, the controller 400 of the portable terminal 2 determines whose optical head 100 is mounted based on the unique information received through the electronic apparatus 1 and previously stored information.

Further, previously captured information may be differently stored according to users and thus useful. For instance, an angle of capturing an image of a mole in a wrist of a user A and a distance from the wrist may be different from an angle of capturing an image of an eyeball of a user B and a distance from the eyeball. When the optical head 100 corresponding to the dermatoscope is mounted for the user A, the focal length of the electronic apparatus 1 may be adjusted corresponding to the capturing angle and distance for the user A.

Further, the optical heads 100 may be minutely different in the size of the opening, the focal length of the lens section 500, etc. even though they are of the same kind. The optical head 100 may store these pieces of information in the storage 505, and provide the information to the electronic apparatus 1 so that the electronic apparatus 1 can control the lens control section 1007 to adjust the first and second lens sections 1000a and 1000b based on the information received from the mounted optical head 100. Further, the electronic apparatus 1 may provide the received information to a user through the display 1400 of the electronic apparatus 1.

Figure 27:
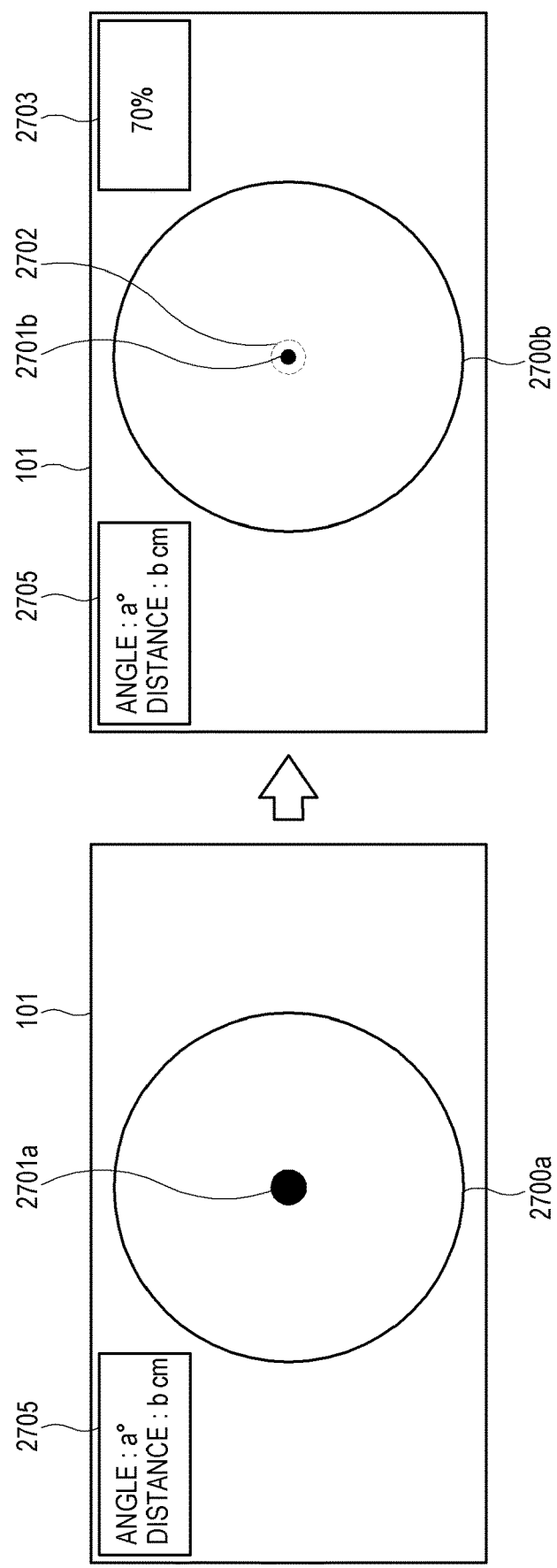
FIG. 27 shows an example of providing a progress captured according to one embodiment of the present invention.
Figure 28:
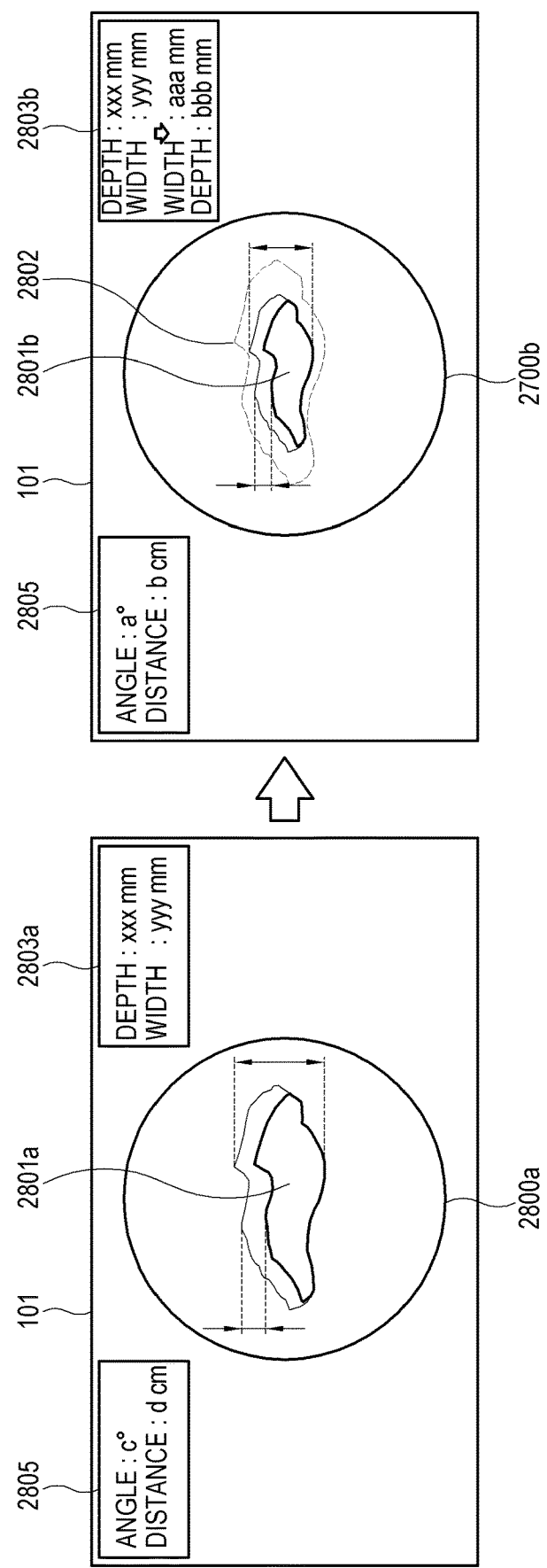
FIG. 28 shows an example of providing a progress captured according to one embodiment of the present invention.

FIGS. 27 and 28 show examples of providing a progress captured according to one embodiment of the present invention.

Referring to FIG. 27, when a user who has a mole on a skin takes an image of the mole leaving a time lag, the image of the user's skin, information for helping image capturing, and information based on the time lag are provided. When a user mounts the optical head 100a corresponding to the dermatoscope to the electronic apparatus 1 and controls the portable terminal 2 to capture an image of a skin mole 701, the controller 400 of the portable terminal 2 transmits a control signal to the electronic apparatus so that light can be emitted to a user's skin, and the electronic apparatus 1 emits light to the user's skin though the mounted optical head 1000 and provides light reflected from the user's skin to the camera 200.

When the camera 200 converts the received light into an image, the display 101 may display an image 2700a of the skin including the mole 2701a, and information 2705 including an angle at which the portable terminal 2 captures the image, a distance from a user's body part, etc.

When a user takes an image of the skin again after some time elapses from when taking the image, the display 101 may display an image 2700b of the current skin including the mole 2701b changed in size together with an afterimage 2702 of a mole 2701a at the previous capturing, and information 2705 including an angle of the portable terminal 2 and a distance from a user's body part when the portable terminal 2 captures the image. The controller 400 of the portable terminal 2 compares and analyzes the mole 2701a at the previous capturing and the mole 2701b of the current skin, and controls the display 101 to provide information 2703 about what percentage the mole is reduced in size, i.e. heals over.

To more correct comparison in the size of the mole 2701, a user has to take an image of the skin at the same angle and distance as those of the previous capturing with reference to the information 2705 about the angle and distance of the portable terminal 2, and therefore the portable terminal 2 may show a user the relevant information 2705, and may also use a notification sound to inform the user that the angle and distance from the body part for the current capturing are the same as those of previous capturing.

FIG. 28 shows an example of providing an image of capturing a skin, information for helping the capturing, and information based on a time lag when a user who has a wound on the skin takes an image of the skin leaving the time lag.

When a user controls the portable terminal 2 to capture an image of a skin wound 2100, the controller 400 of the portable terminal 2 controls the display 101 to provide an image 2800a obtained by capturing the skin including the wound 2801a, information 2805 about an angle and distance from a user's body part at which the portable terminal 2 captures the image, and information 2803a about the depth and width of the wound 2100 based on an analysis of the captured image.

When a user takes an image of the skin wound 2100 after some time elapses, the controller 400 of the portable terminal 2 controls the display 101 to provide an image 2700b of the current skin including the wound 2801b together with an afterimage 2802 of the wound 2801a at the previous capturing, information 2805 including an angle of the portable terminal 2 and a distance from a user's body part when the portable terminal 2 captures the image, and information 2803 about the depth and width of the wound 2100 by analyzing the captured image. The information 2803b about the depth and width may include progress information so that the depth and width of the wound 2801b at the current capturing can be compared with the depth and width of the wound 2801a at the previous capturing.

Figure 29:
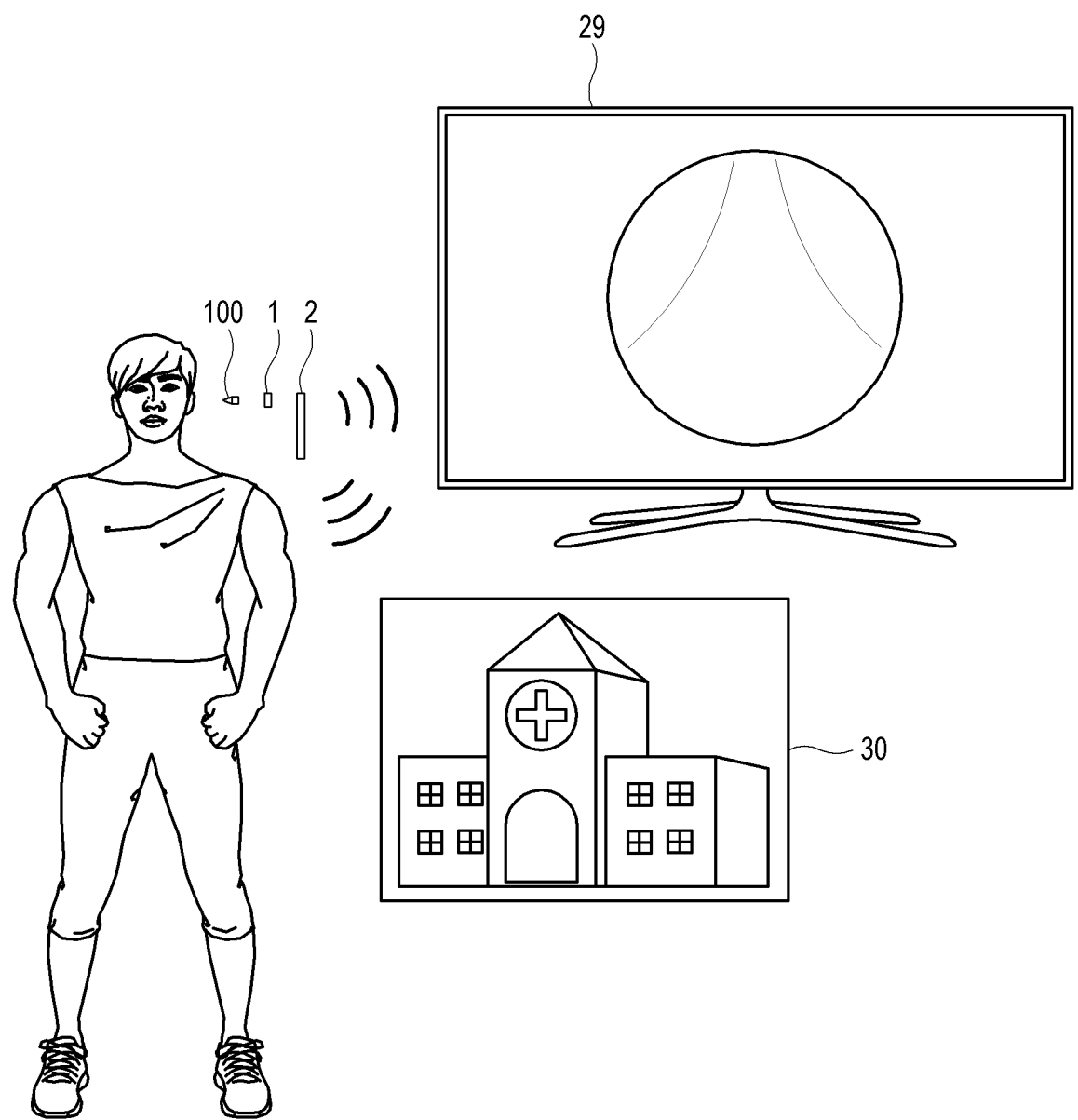
FIG. 29 shows an example of using a portable terminal and an electronic apparatus according to one embodiment of the present invention.

FIG. 29 shows an example of using a portable terminal and an electronic apparatus according to one embodiment of the present invention.

The portable terminal 2 may include the communicator 401 to communicate with an external apparatus 29. The controller 400 controls the communicator 401 to transmit an image of a user's body part captured using the optical head 100 and the electronic apparatus 1 to the outside.

The outside includes a separate display apparatus 29 for displaying the received image, an external hospital 30, etc.

The display apparatus 29 includes a display panel larger than the display 101 of the portable terminal 2, so that the captured image can be seen through a larger screen. Further, the captured image is transmitted to the hospital or the like external diagnosis facility so that a user can be remotely diagnosed without going to the hospital.

Figure 30:
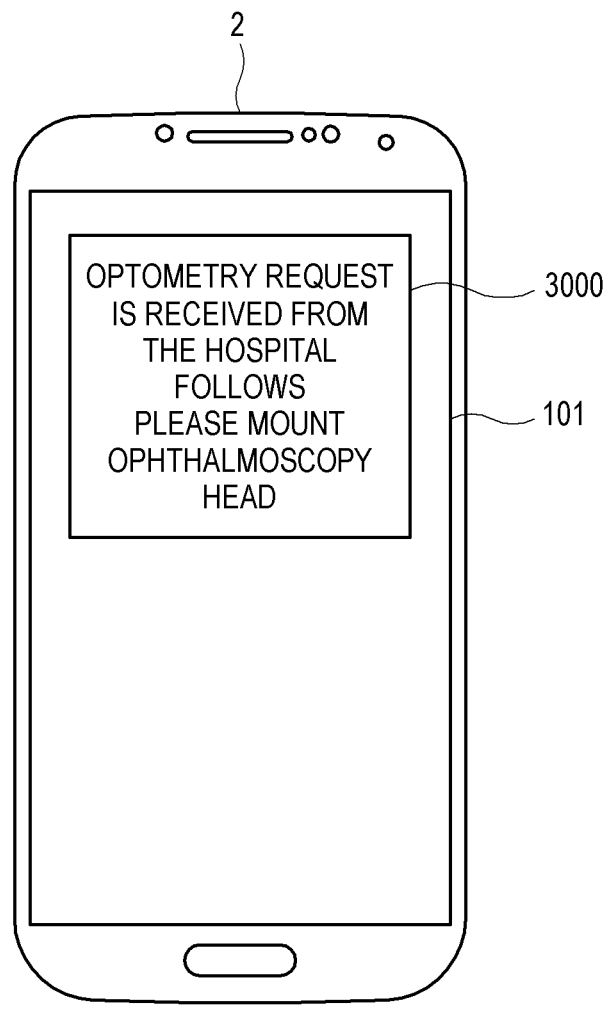
FIG. 30 shows a UI of a diagnosis request received from the outside according to one embodiment of the present invention.

FIG. 30 shows a UI of a diagnosis request received from the outside according to one embodiment of the present invention.

As described above, when a user selects at least one among a plurality of menus items corresponding to a plurality of examinations through the UI, the controller 400 of the portable terminal 2 may control the display 101 to provide the guide information for capturing an image of a user's body part so as to perform examination corresponding to the selected menu item.

According to another embodiment of the present invention, a medical examination service supported by the portable terminal 2 may start in response to an examination request received from the hospital or the like outside. When the portable terminal 2 is requested by the outside to perform a certain examination, the display 101 may display guide information for guiding a user to capture an image, which includes a guide 3000 for proposing the requested examination to be carried out, and information about the optical head 100 to be mounted. The examination request received from the outside may include the guide information provided to a user. The guide information received from the outside may include information about a specific optical head 100, a distance between the body part and the portable terminal 2, an angle of the portable terminal 2, an after image of a previously captured image corresponding to a previous examination request, etc.

When a user controls the portable terminal 2 and the electronic apparatus 1 to capture an image of a user's body part with reference to the guide information, the controller 400 of the portable terminal 2 may control the communicator 401 to transmit the captured image to the outside that makes the request for the examination.

Figure 31:
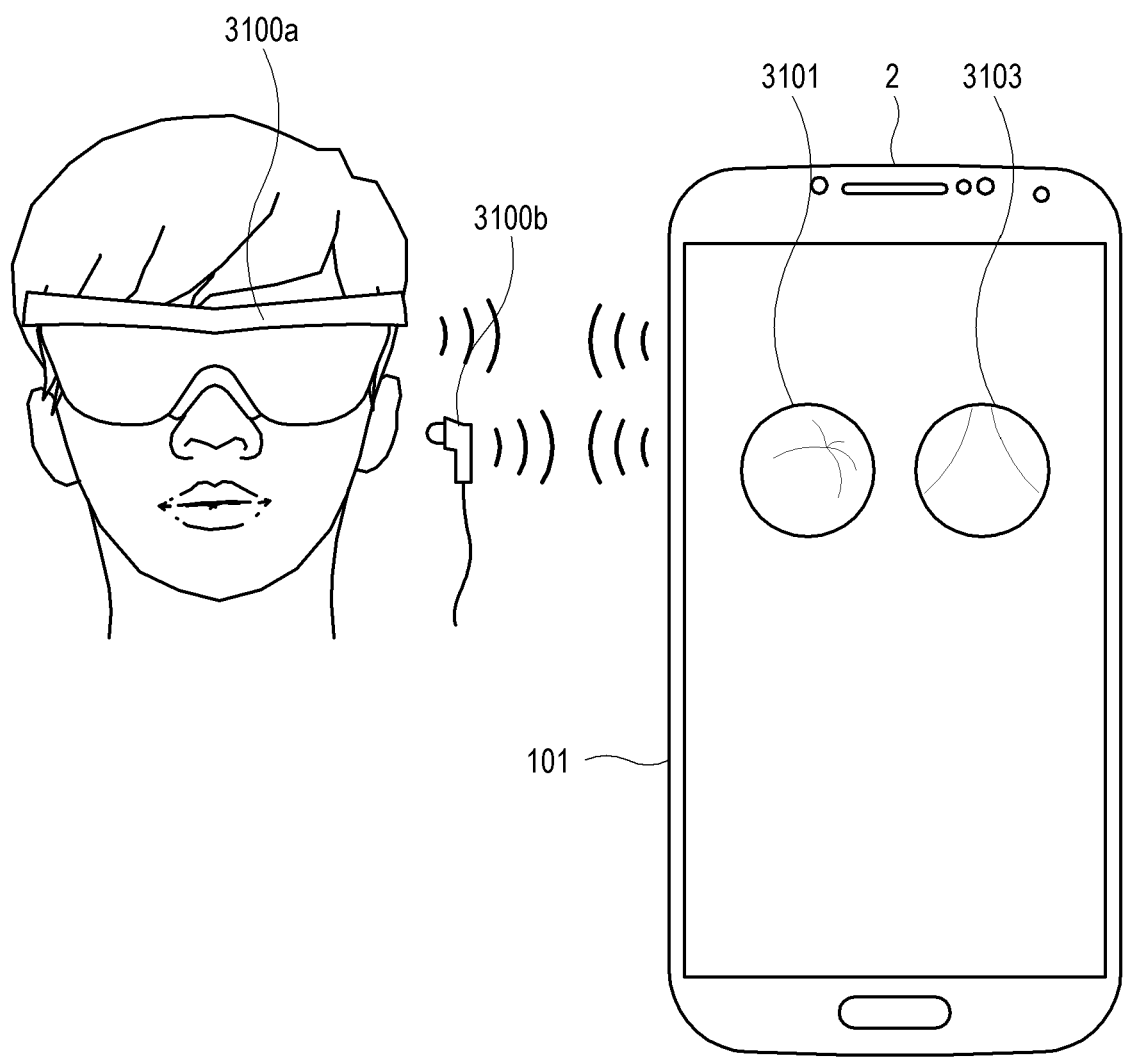
FIG. 31 shows an example of a portable terminal and an electronic apparatus according to another embodiment of the present invention.
Figure 32:
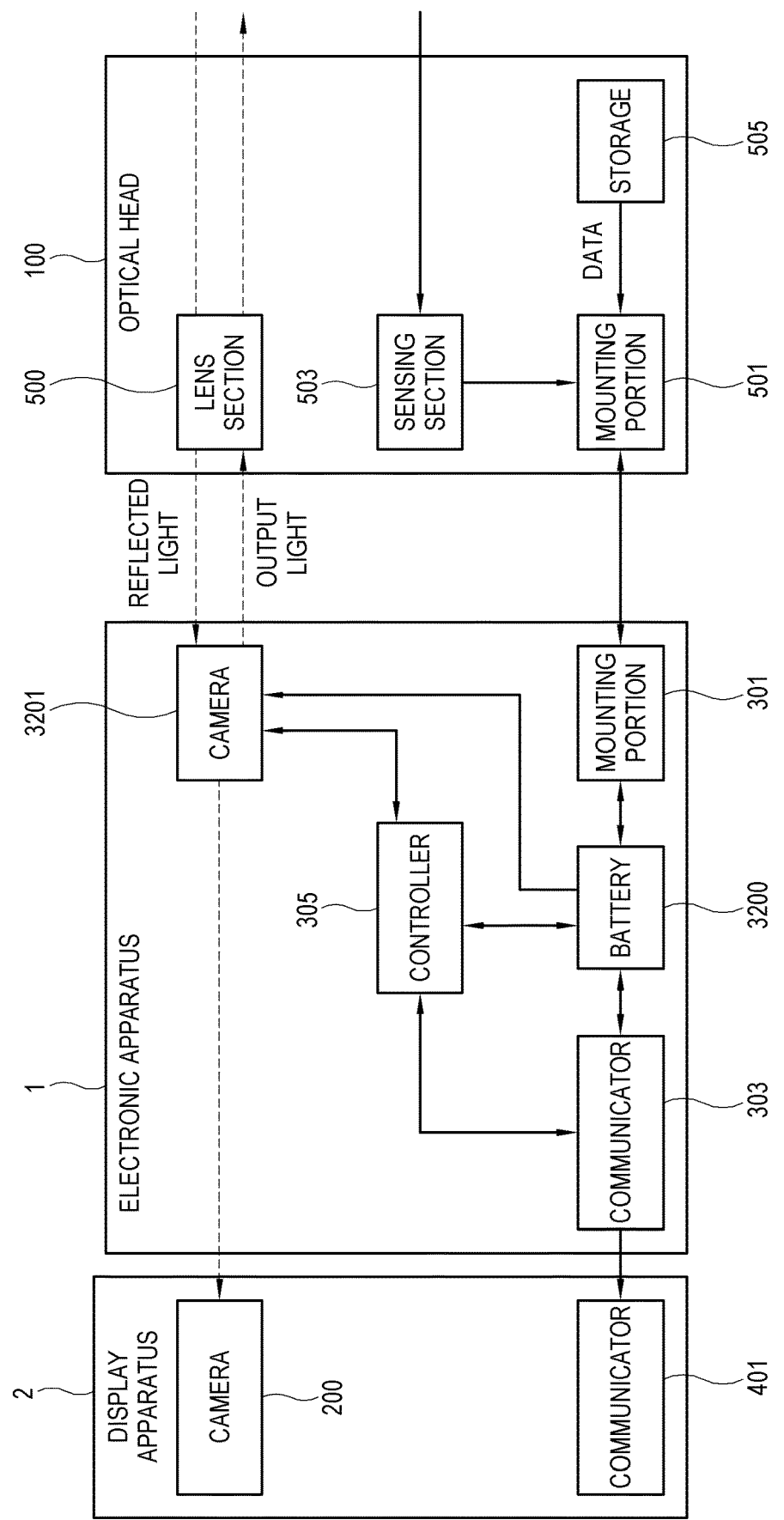
FIG. 32 shows an example of a portable terminal and an electronic apparatus according to another embodiment of the present invention.

FIGS. 31 and 32 show examples of a portable terminal and an electronic apparatus according to another embodiment of the present invention.

In the foregoing description, the electronic apparatus is directly coupled to the portable terminal 2 and operates by receiving power from the power terminal of the portable terminal 2, and light reflected from a user's body part is transmitted to the camera 200 of the portable terminal 2.

Alternatively, the electronic apparatus 1 according to another embodiment of the present invention may operate without receiving power from the portable terminal 2, and a directly captured image is transmitted to the portable terminal 2 by communication. To this end, the electronic apparatus 1 may further include a battery and a camera, and may be materialized by a wearable device such as a smart goggle, an ear phone, a head-mounted display, etc. as shown in FIG. 31.

Referring to FIG. 31, a user may control the portable terminal 2 to capture a body part while wearing wearable devices 3100a and 3100b, and the wearable devices 3100a and 3100b may be configured to transmit the captured image to the portable terminal 2. The portable terminal 2 is configured to display a use's eyeball image 3101 and inner ear image 3103, which are received from the wearable devices 3100a and 3100b, on the display 101.

The wearable devices 3100a and 3100b may be configured to include separate batteries, and a power terminal for receiving power from the portable terminal 2 by a wire/wirelessly. The wearable devices 3100a and 3100b are driven by receiving power from the portable terminal 2 through a signal wire, the image may be transmitted to the portable terminal 2 through the connected signal wire.

FIG. 32 shows a block diagram of the portable terminal 2, the electronic apparatus 1 and the mounted optical head 100 according to another embodiment of the present invention. As described above, the electronic apparatus 1 may include a battery 3200 and a camera 3201.

The battery 3200 is charged with power received from the outside, and supplies the charged power to the electronic apparatus 1.

The camera 3201 employs the mounted optical head 100 to capture an image of a user's body part, and generates an image by converting light received through the optical head 100. The camera 3201 may include a converter for converting the reflected light received through the optical head 100 into the image based on an electric signal.

The electronic apparatus 1 and the optical head 100 are mounted using the mounting portions 301 and 501, the identification information of the mounted optical head 100 is transmitted to the portable terminal 2. The camera 3201 of the electronic apparatus 1 is configured to capture an image of a user's body part and generate an image when a control signal based on the identification information is transmitted from the portable terminal 2 to the electronic apparatus 1. The generated image may be transmitted to the portable terminal 2 through the communicator 401, or may be directly transmitted to the camera 200 of the portable terminal 2. Further, the display 101 of the portable terminal 2 may be configured to display the image received from the electronic apparatus 1.

Figure 33:
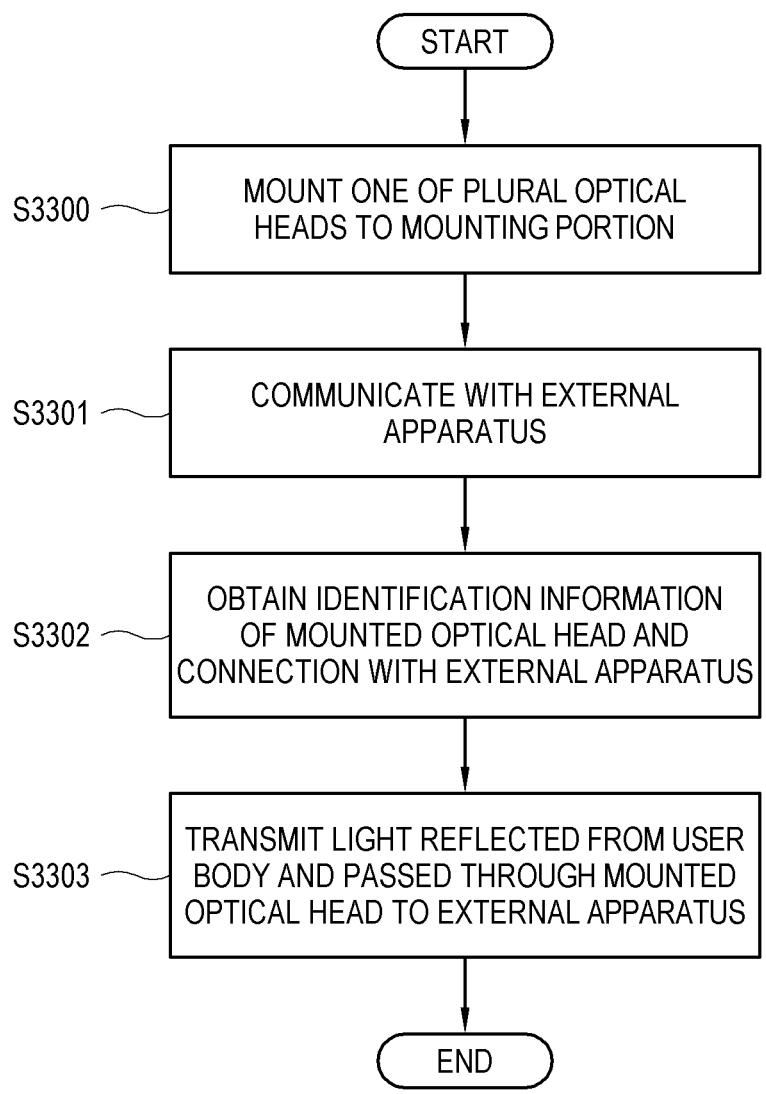
FIG. 33 is a flowchart of controlling an electronic apparatus according to one embodiment of the present invention.

FIG. 33 is a flowchart of controlling an electronic apparatus according to one embodiment of the present invention.

First, at operation S3300, one among the plurality of optical heads 100 is mounted to the mounting portion 501 of the electronic apparatus 1. At operation S330, the electronic apparatus 1 communicates with an external apparatus 2, i.e. the portable terminal 2 through the communicator 303. At operation S3302 the communicator 303 obtains the identification information of the mounted optical head 100, and transmits the obtained information to the external apparatus. Last, at operation S330, the optical module 300 transmits light reflected from a user's body part and passed through the mounted optical head 100 to the camera 200 of the external apparatus 2.

Figure 34:
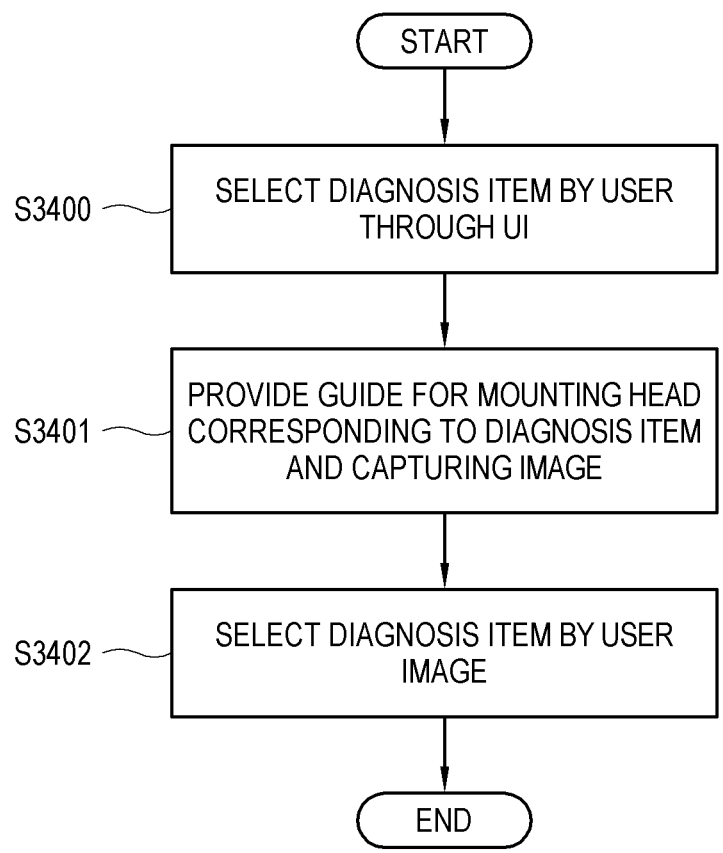
FIG. 34 is a flowchart of controlling a portable terminal according to one embodiment of the present invention.

FIG. 34 is a flowchart of controlling a portable terminal according to one embodiment of the present invention.

First, at operation S3400, a user controls a displayed UI to select an item desired to be diagnosed. At operation S3401, the controller 400 of the portable terminal 2 controls the display 101 to provide guide information about the optical head 100 corresponding to the diagnosis item and image capturing. Last, at operation S3402, the controller 400 controls the display 101 to output and provide the captured image.

Figure 35:
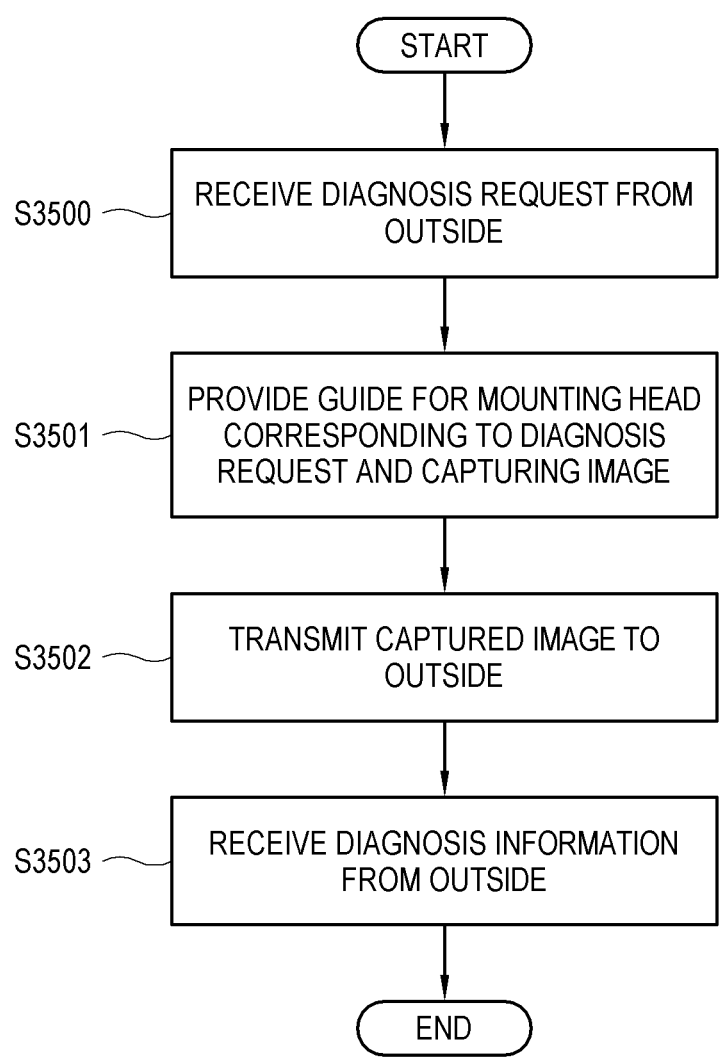
FIG. 35 is a flowchart of controlling a portable terminal when a diagnosis request is received from the outside according to one embodiment of the present invention.

FIG. 35 is a flowchart of controlling a portable terminal when a diagnosis request is received from the outside according to one embodiment of the present invention.

First, at operation S3500, the communicator 401 of the portable terminal 2 receives an examination and diagnosis request from the outside. At operation S3501, the controller 400 controls the display 101 to provide the guide information about the optical head 100 to be mounted corresponding to the received diagnosis request and the image capturing. Then, at operation S3502, the controller 400 controls the communicator 401 to transmit the image captured by the camera 200 using the electronic apparatus 1 and the optical head 100 to the outside that makes the request for the examination and the diagnosis. Last, at operation S3503, the communicator 401 receives diagnosis information from the outside, and the controller 400 controls the display 101 to provide the received information to a user.

Figure 36:
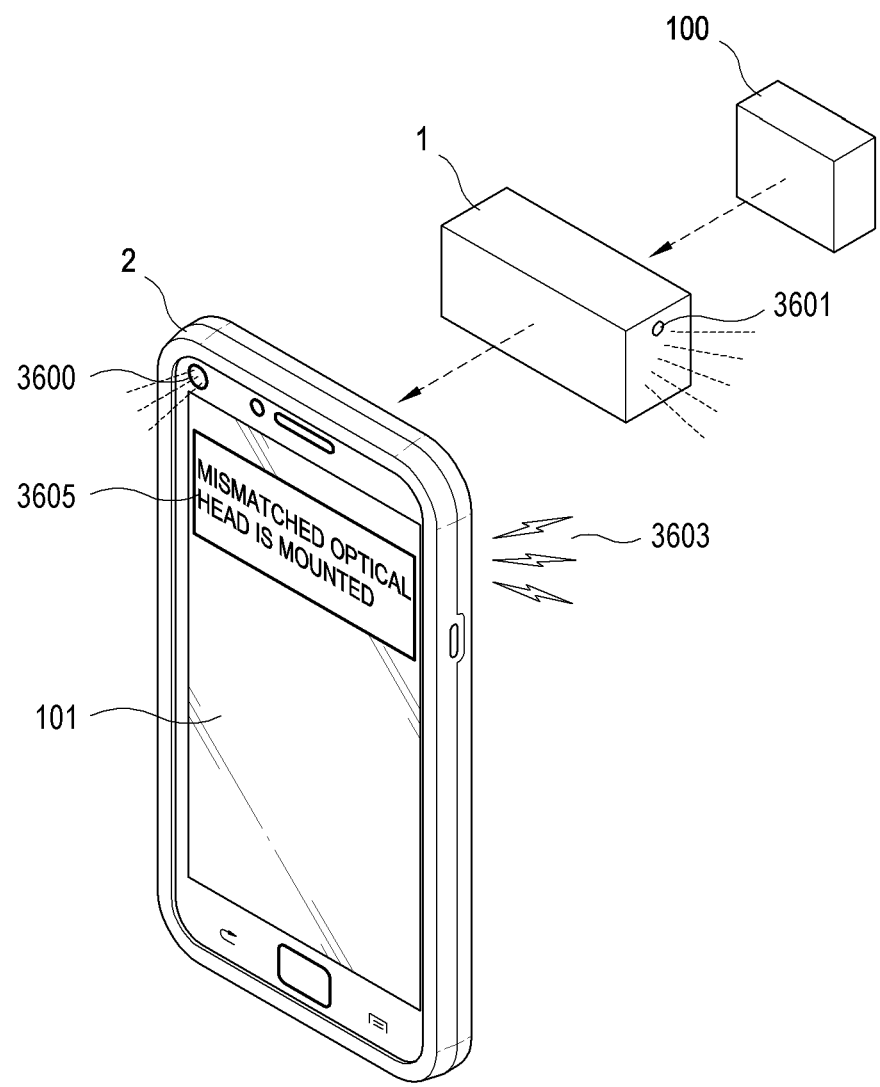
FIG. 36 shows an example that a portable terminal and an electronic apparatus warn of a wrong mount of an optical head according to one embodiment of the present invention.
Figure 37:
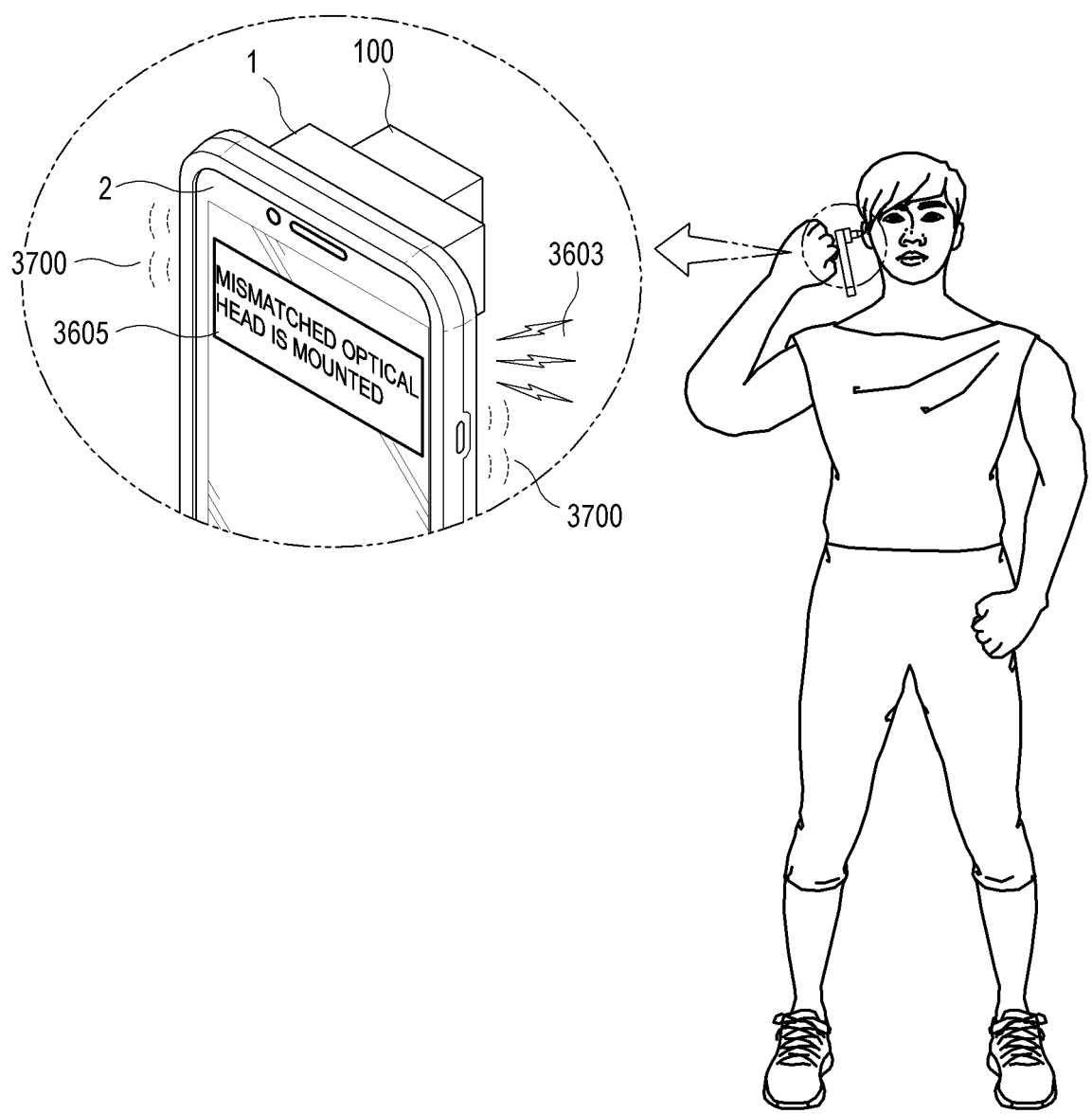
FIG. 37 shows an example that a portable terminal and an electronic apparatus warn of a wrong mount of an optical head according to one embodiment of the present invention.

FIGS. 36 and 37 show examples that a portable terminal and an electronic apparatus warn of wrong mount of an optical head according to one embodiment of the present invention.

After a user selects an item to be diagnosed or a diagnosis request is received from the outside, a user mounts the optical head 100 to the electronic apparatus 1 based on the provided guide information. Then, the identification information of the optical head 100 is provided to the portable terminal 2 via the electronic apparatus 1, and the portable terminal 2 determines whether the optical head 100 mounted to the electronic apparatus 1 corresponds to the user's selection or the diagnosis request from the outside. When the mounted optical head 100 does not correspond to the selection, the display 101 may provide a UI including guide items 3605 and 3703.

The electronic apparatus 1 and the portable terminal 2 may also include LED lamps 3600 and 3601. When the mounted optical head 100 is different from that corresponding to a user's selection or the external request, the LED lamps 3600 and 3601 emit red light. When the matched optical head 100 is mounted, blue light may be emitted.

Further, the electronic apparatus 1 and the portable terminal 2 may use warning sounds 3603 and 3601 or the like sound and vibration 370 to guide a user to mount the matching optical head 100.

In this embodiment, at least one of the electronic apparatus 1 and the portable terminal 2 may include the sensing section such as a gyroscope, an accelerometer, and a geomagnetic sensor, etc. and the portable terminal 2 may use the sensing section to sense a user's posture.

For example, when a user mounts the mismatched optical head 100, the portable terminal 2 and the electronic apparatus 1 primarily warn a user of the mismatched optical head 100 through the LED lamps 3600 and 3601, and the guide items 3605 and 3703. Then, when it is sensed that a user moves the portable terminal 2 to capture an image of a user's body part with the mismatched optical head 100, the portable terminal 2 may make the vibration 3700 or the warning sound 3603 and 3601. To this end, the portable terminal 2 and the electronic apparatus 1 may include a loudspeaker to output the sound, and a motor to make the vibration.

The present invention is not limited to the accompanying drawings and the foregoing descriptions, and may be variously embodied to make a user mount a matched optical head 100. According to another embodiment of the present invention, the mounting portion 301 of the electronic apparatus 1 may prevent the optical head 100, which mismatches with a user's selection or a diagnosis request from the outside, from being mounted under control of the portable terminal 2. When the identification information of the optical head 100 is transmitted to the portable terminal 2 through temporary coupling with the optical head 100, and the portable terminal 2 determines that the mismatched optical head 100 is mounted and transmits a control signal to the electronic apparatus 1, the controller 305 may control the mounting portion 301 to prevent the mismatched optical head 100 from being mounted to the electronic apparatus 1.

Figure 38:
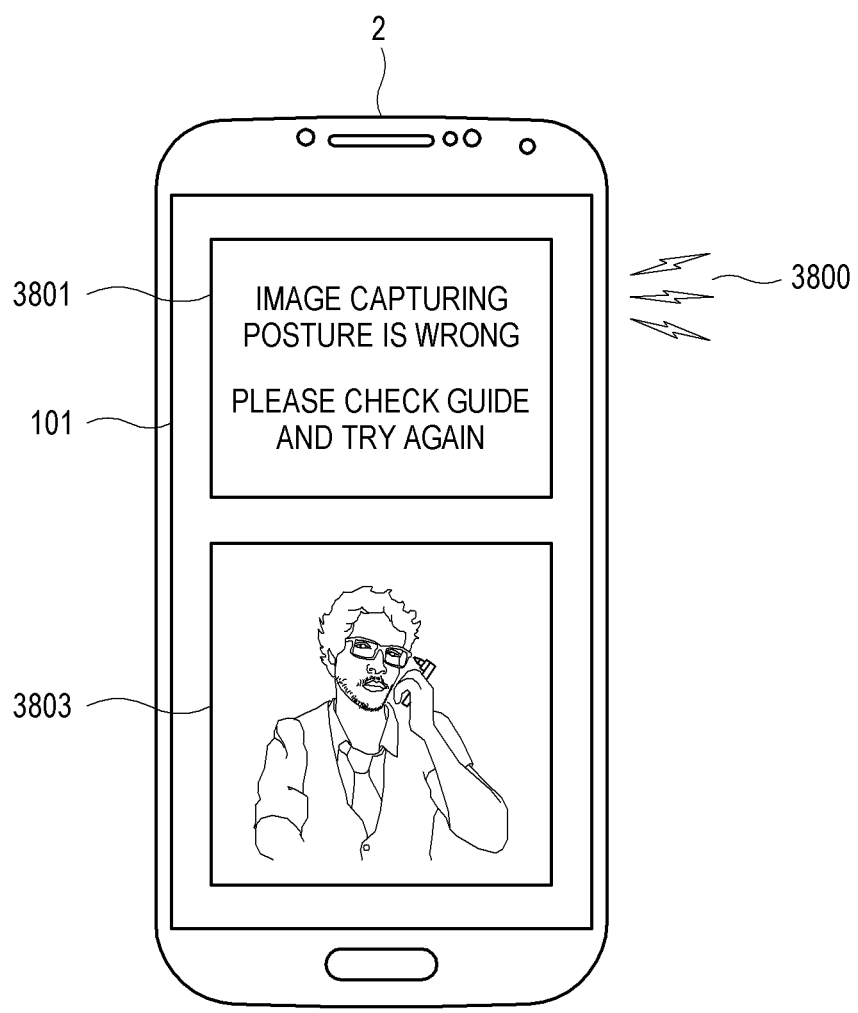
FIG. 38 shows an example that a portable terminal according to one embodiment of the present invention provides guide information when a body is captured in wrong posture.

FIG. 38 shows an example of sensing a user's image taking posture and providing guide information again according to one embodiment of the present invention.

As described above, at least one of the electronic apparatus 1 and the portable terminal 2 may include the sensing section including a gyroscope, a geomagnetic sensor, and accelerometer. The portable terminal 2 is capable of sensing a user's posture based on information sensed by the sensing section. When the sensed posture is of a user's selection, or when it is not suitable for capturing an image of a body part on the basis of a diagnosis requested by the outside, a guide item 3801 for notifying of a wrong image capturing posture and guide information 3803 for notifying of a correct image capturing posture may be provided as a UI through the display 101, and provided as a sound 3800 through the loudspeaker.

Figure 39:
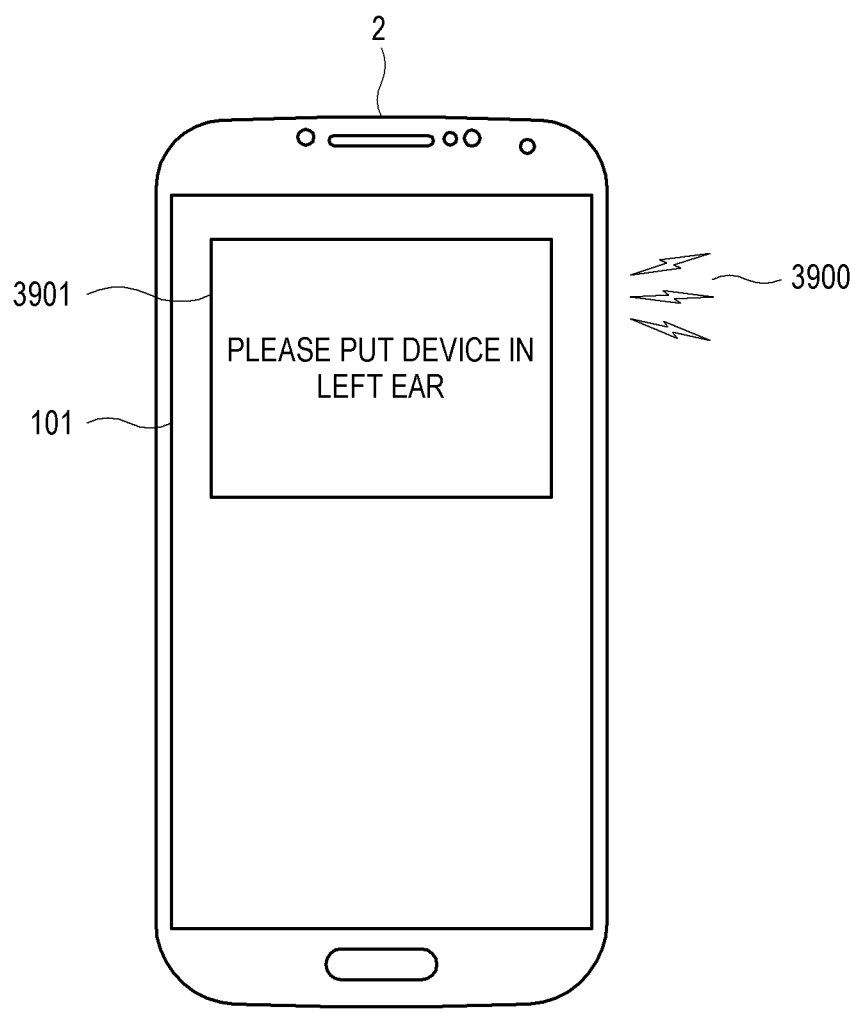
FIG. 39 shows an example that a portable terminal according to one embodiment of the present invention gives a guide to a correct body part when a wrong body part is captured.

FIG. 39 shows an example that a portable terminal according to one embodiment of the present invention gives a guide to capture an image of a correct body part.

When a user takes an image of a body part in response to the user's selection or an external request, but the captured image of the body part is different from that corresponding to the user's selection or the external request, the portable terminal 2 may provide the guide item 3901 for advising a user to try again as a UI through the display 101 or as a sound 3900 through the loudspeaker.

To determine whether an image of a body part is captured in response to a user's selection or an external request, the captured image may be analyzed, or a user's posture may be determined using the sensing section.

For instance, it is possible to determine whether a user takes an image a skin or an ear based on whether the portable terminal 2 is arranged horizontally or vertically. Further, it is possible to determine whether a user takes an image of a left ear or a right ear based on an orientation of the portable terminal 2, thereby providing relevant information to a user.

The portable terminal 2 may also compare the captured image with the previously captured image and determine whether a user's image taking distance and position are the same as those of previous image capturing. When an image of a wrong body part is being captured, relevant information may be provided to a user so as to capture an image of a correct body part.

For example, the portable terminal 2 may provide the guide information for advising a user to capture an image of a wrist in order to diagnose change in size of a mole between the previously captured image and the image captured again, and determine whether the user captures an image of the same wrist as that of the previous image capturing by generally comparing the previously captured wrist image and the currently captured wrist image as well as the targeted specific point of the wrist. When it is determined based on similarity that a user takes an image of a correct body part, the user may be informed of that by various methods such as green light emitted from the LED lamp 3600, the notification sound 3603, the UI displayed on the display 101, etc. On the other hand, when it is determined that a user takes an image of a wrong body part, the user may be informed of that by red light emitted from the LED lamp 3600, the notification sound 3603, the UI displayed on the display 101, vibration 3700, etc. The user can correctly mount the optical head 100 through the guide information and such appended outputs provided by the portable terminal 2, take a correct posture, and correctly captures an image of a body part, thereby diagnosing a disease of the body part.

Although a few embodiments of the present invention have been described in detail, the present invention is not limited to these embodiments and various changes can be made without departing from the scope of the appended claims.

The invention claimed is:

1. An electronic apparatus comprising:
   a first mounting portion to which one of a plurality of optical heads is selectively mountable;
   a second mounting portion to which an external apparatus is mountable;
   a communication interface configured to communicate with the external apparatus mounted to the second mounting portion;
   an optic comprising a light source and a plurality of lenses, the optic being configured to emit light through the optical head mounted to the first mounting portion, receive light which is reflected from a user's body through the optical head mounted on the first mounting portion, and transmit the received light to a camera of the mounted external apparatus;
   a sensor configured to sense a distance and an angle from the user's body to the electronic apparatus;
   a storage configured to store the distance and the angle sensed by the sensor; and
   a controller configured to:
   based on one of the plurality of optical heads being mounted to the first mounting portion, obtain identification information about the optical head mounted to the first mounting portion;

control the communication interface to transmit the identification information to the mounted external apparatus;

select at least one lens among the plurality of lenses and adjust a focal length of the selected at least one lens by adjusting a location of each lens of the selected at least one lens, based on the identification information;

identify a user corresponding to the identification information, and adjust the focal length of the selected at least one lens based on a distance and an angle previously captured by the identified user and stored in the storage; and in response to a control signal being received, corresponding to the transmitted identification information, from the mounted external apparatus through the communication interface, control the light source to generate the emitted light having a pattern indicated by the control signal.

2. The electronic apparatus according to claim 1, wherein the controller is configured to perform communication pairing with the mounted external apparatus though the communication interface based on the electronic apparatus and the mounted external apparatus being within a preset range, and transmit the identification information of the optical head mounted to the first mounting portion to the mounted external apparatus through the communication interface when the communication pairing is completed.

3. The electronic apparatus according to claim 1, further comprising a display, wherein the controller is configured to control the display to display information about a current state of the electronic apparatus.

4. The electronic apparatus according to claim 3, wherein the information about the current state of the electronic apparatus comprises at least one of information about whether the electronic apparatus is communicating with the mounted external apparatus and information about the optical head mounted to the first mounting portion.

5. The electronic apparatus according to claim 1, wherein the first mounting portion comprises a connection terminal for connecting with the mounted optical head, and the controller is configured to receive the identification information from the mounted optical head through the connection terminal.

6. The electronic apparatus according to claim 1, wherein the optic comprises a lens section comprising the plurality of lenses for transmitting incident light; and a lens control section configured to adjust the focal length of the lens section, wherein the controller is further configured to control the lens control section to adjust the focal length of the lens section in response to another control signal received from the mounted external apparatus.

7. The electronic apparatus according to claim 6, wherein the focal length of the lens section is adjusted by at least one of change in distance between the plurality of lenses, and replacement of one of the plurality of lenses by another lens having a different thickness, size, or refractive index.

8. The electronic apparatus according to claim 1, wherein the controller controls the light source to adjust at least one of brightness and chromaticity of the generated emitted light.

9. A method of controlling an electronic apparatus comprising a first mounting portion to which one of a plurality of optical heads is selectively mountable, a second mounting portion to which an external apparatus is mountable, a sensor, a storage, and an optic comprising a light source and a plurality of lenses, the method comprising:

mounting the external apparatus to the second mounting portion;

mounting one of the plurality of optical heads to the first mounting portion;

communicating with the mounted external apparatus;

based on the one of the plurality of optical heads being mounted to the first mounting portion, obtaining identification information of the mounted optical head;

transmitting the identification information to the mounted external apparatus;

selecting at least one lens among the plurality of lenses and adjust a focal length of the selected at least one lens by adjusting a location of each lens of the selected at least one lens, based on the identification information, identifying a user corresponding to the identification information, and adjust the focal length of the selected at least one lens based on a distance and an angle previously captured by the identified user through the sensor and stored in the storage, and in response to a control signal being received, corresponding to the transmitted identification information, from the mounted external apparatus through a communication interface, generating, by the light source, output light that is emitted through the optical head mounted to the first mounting portion, the output light having a pattern indicated by the control signal;

receiving light which is reflected from the identified user's body through the optical head mounted on the first mounting portion; and transmitting the received light to a camera of the mounted external apparatus.

10. The method according to claim 9, wherein the communicating with the mounted external apparatus comprises:

performing communication pairing with the mounted external apparatus though the communication interface based on the electronic apparatus and the mounted external apparatus being within a preset range; and transmitting the identification information of the optical head mounted to the first mounting portion to the mounted external apparatus through the communication interface when the communication pairing is completed.

11. The method according to claim 9, further comprising displaying information about a current state of the electronic apparatus through a display.

12. The method according to claim 11, wherein the information about the current state of the electronic apparatus comprises at least one of information about whether the electronic apparatus is communicating with the mounted external apparatus and information about the optical head mounted to the first mounting portion.

* * * * *